(12) United States Patent
Kim et al.

(10) Patent No.: US 11,305,120 B2
(45) Date of Patent: Apr. 19, 2022

(54) MONOLITHIC NEURAL INTERFACE SYSTEM

(71) Applicant: UNIVERSITY OF CENTRAL FLORIDA RESEARCH FOUNDATION, INC., Orlando, FL (US)

(72) Inventors: Brian Kim, Orlando, FL (US); Kevin White, Orlando, FL (US); Geoffrey Mulberry, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 16/765,587

(22) PCT Filed: Nov. 20, 2018

(86) PCT No.: PCT/US2018/061985
§ 371 (c)(1),
(2) Date: May 20, 2020

(87) PCT Pub. No.: WO2019/100055
PCT Pub. Date: May 23, 2019

(65) Prior Publication Data
US 2020/0306539 A1    Oct. 1, 2020

Related U.S. Application Data

(60) Provisional application No. 62/588,605, filed on Nov. 20, 2017.

(51) Int. Cl.
*A61N 1/36* (2006.01)
*A61N 1/05* (2006.01)
(Continued)

(52) U.S. Cl.
CPC ....... *A61N 1/36125* (2013.01); *A61N 1/0529* (2013.01); *A61N 1/375* (2013.01);
(Continued)

(58) Field of Classification Search
CPC .............. A61N 1/36125; A61N 1/0529; A61N 1/37282; A61N 1/37288; A61N 1/375;
(Continued)

(56) References Cited

U.S. PATENT DOCUMENTS 8,560,041 B2 * 10/2013 Flaherty ................... A61B 5/24
600/373
10,433,754 B2 * 10/2019 Nurmikko .......... A61N 1/37229
(Continued)

OTHER PUBLICATIONS

Anderson, G. et al., "Wireless Integrated Circuit for the Acquisition of Electrocorticogram Signals", IEEE 2010, pp. 2952-2955.
(Continued)

*Primary Examiner* — Mallika D Fairchild
*Assistant Examiner* — Minh Duc G Pham
(74) *Attorney, Agent, or Firm* — Timothy H. Van Dyke; Wolter, Van Dyke, Davis PLLC

(57) ABSTRACT

A device comprising monolithic substrates forming a chip including a wireless, battery-less monolithically-integrated neural interface (MINI) device. The chip comprises an integrated circuit (IC) being embedded in a first monolithic substrate and comprising a plurality of amplifiers configured to amplify received neural signals from a monitored subject, and a radio data signal generator configured to process the amplified neural signals and generate a multiplexed digital signal. The chip includes radio-frequency (RF) planar coils embedded in a second monolithic substrate, being electrically connected to the IC through the first monolithic substrate, being configured for wireless transmission of the multiplexed digital signal to a remote wireless device and being configured to receive wireless power signals to power (Continued)

the IC. A plurality of on-chip electrodes is included to directly sense the neural signals of the subject and provide the neural signals to the plurality of amplifiers.

22 Claims, 21 Drawing Sheets

(51) Int. Cl.
| | |
|---|---|
| *A61N 1/372* | (2006.01) |
| *A61N 1/375* | (2006.01) |
| *A61N 1/378* | (2006.01) |
| *A61N 1/40* | (2006.01) |

(52) U.S. Cl.
CPC ....... *A61N 1/3787* (2013.01); *A61N 1/37282* (2013.01); *A61N 1/37288* (2013.01); *A61N 1/40* (2013.01)

(58) Field of Classification Search
CPC .......... A61N 1/3787; A61N 1/40; A61N 1/02; A61N 1/3605
See application file for complete search history.

(56) References Cited

U.S. PATENT DOCUMENTS

| | | | |
|---|---|---|---|
| 2001/0028108 A1* | 10/2001 | Higashi | H01L 23/3171 257/735 |
| 2005/0277999 A1 | 12/2005 | Strother et al. | |
| 2006/0074460 A1* | 4/2006 | Maghribi | A61N 1/0543 607/53 |
| 2006/0173259 A1 | 8/2006 | Flaherty et al. | |
| 2009/0301994 A1* | 12/2009 | Bhandari | A61B 5/685 216/11 |
| 2014/0094674 A1 | 4/2014 | Nurmikko et al. | |
| 2015/0094786 A1* | 4/2015 | Deterre | A61N 1/3756 607/61 |

OTHER PUBLICATIONS

Borton, David A. et al., "An Implantable Wireless Neural Interface for Recording Cortical Circuit Dynamics in Moving Primates", J. Neural Eng., 2013, 25 pages.

Capogrosso, Marco et al., "A brain-spine interface alleviating gait deficits after spinal cord injury in primates", Nature, 2016, vol. 539, pp. 284-306.

Darie, Radu et al., "Delivering the Sense of Touch to the Human Brain", Neuron, 2017, vol. 93, pp. 728-730.

Kim, Brian Namghi et al., "Parallel Recording of Neurotransmitters Release from Chromaffin Cells Using a 10×10 CMOS IC Potentiostat Array with On-Chip Working Electrodes", Biosens Bioelectron. Mar. 15, 2013; vol. 41, pp. 736-744.

Lebedev, Mikhail A. et al., "Future developments in brain-machine interface research", Clinics 2011, vol. 66, pp. 25-32.

Lebedev, Mikhail A. et al., "Toward a whole-body neuroprosthetic", Progress in Brain Research, 2011, vol. 194, pp. 47-60.

Maynard, Edwin M. et al,"The Utah Intracortical Electrode Array: a recording structure for potential brain-computer Interfaces", Electroencephalography and clinical Neurophysiology 102 (1997) 228-239.

Mestais, Corrine S. et al, "WIMAGINE: Wireless 64-Channel ECoG Recording Implant for Long Term Clinical Applications", IEEE Transactions on Neural Systems and Rehabilitation Engineering, vol. 23, No. 1, Jan. 2015, pp. 10-21.

Muller, Jan et al., "High-resolution CMOS MEA platform to study neurons at subcellular, cellular, and network levels", Lab Chip, 2015, vol. 15, pp. 2767-2780.

Rothbert, Jonathan M. et al., "An integrated semiconductor device enabling non-optical genome sequencing", Nature 2011, vol. 475, pp. 348-352.

Schwarz, David A. et al., "Chronic, Wireless Recordings of Large Scale Brain Activity in Freely Moving Rhesus Monkeys", Nat Methods, 2014, vol. 11, 31 pages.

White, Kevin A. et al., "Multifunctional High-Throughput Single-Cell Analysis using Reconfigurable Amplifier Array", 2269-Pos Board B589, 2016, 1 page.

Yin, Ming et al., "Wireless Neurosensor for Full-Spectrum Electrophysiology Recordings during Free Behavior", Neuron, 2014, vol. 84, pp. 1170-1182.

CA3083143; Office Action, dated Jul. 2020, 4 pages.

PCT/US2018/061985; International Search Report and Written Opinion; dated Apr. 12, 2019, 14 pages.

Harrison, Reid R. et al., "Designing Efficient Inductive Power Links for Implantable Devices", 4 pages.

Tang, Wei et al. "A Pulse-based Amplifier and Data Converter for Bio-potentials", 4 pages.

Kim, Brian Namghi et al., "Parallel Recording of Neurotransmitters Release from Chromaffin Cells Using a 10×10 CMOS IC Potentiostat Array with On-Chip Working Electrodes", Biosen Bioelectron, Mar. 15, 2014, 19 pages.

White, Kevin A. et al., "Multifunctional High-Throughput Single-Cell Analysis using Reconfigurable Amplifier Array", 2269-Pos, Board B589, Feb. 14, 2017, p. 461a.

Harrison, Reid R., "Wireless Neural Recording With Single Low-Power Integrated", IEEE Trans Neural Syst Rehabil Eng. Aug. 2009, vol. 17, No. 4, 25 pages.

Rogers, Christy L. et al., "A Pulse-Based Feature Extractor for Spike Sorting Neural Signals", 4 pages.

* cited by examiner 10A
10B
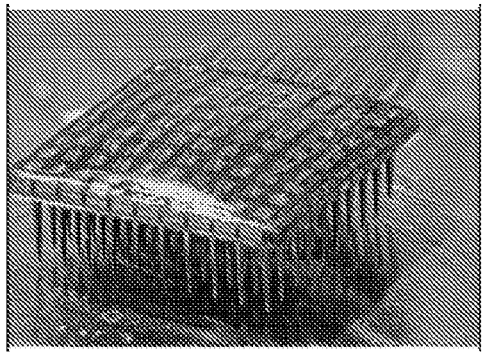
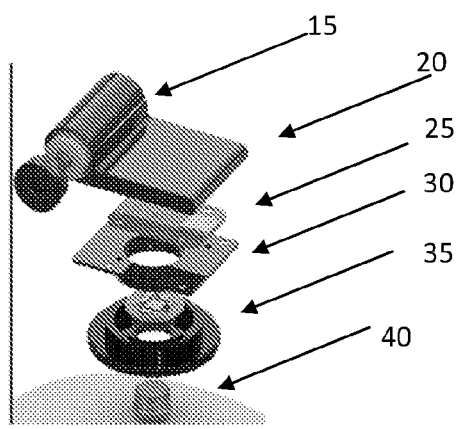
FIG. 1A
FIG. 1B

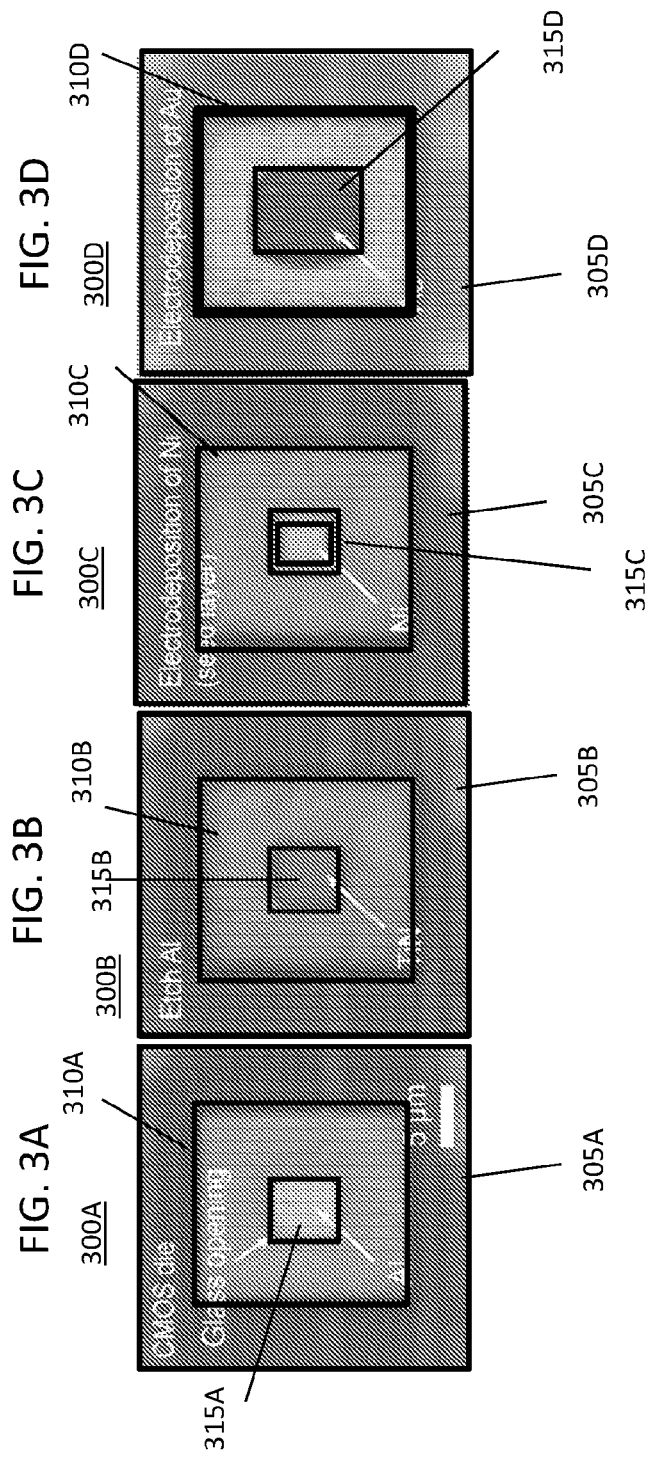

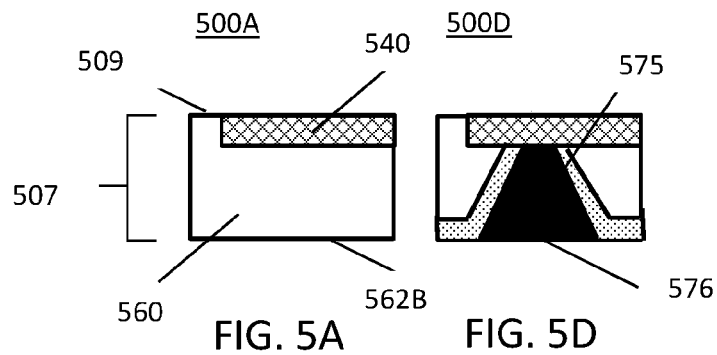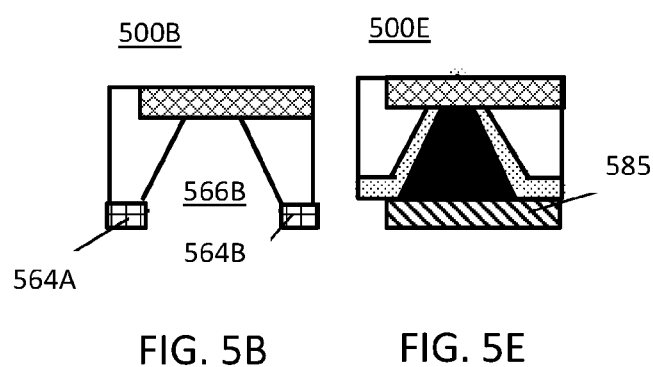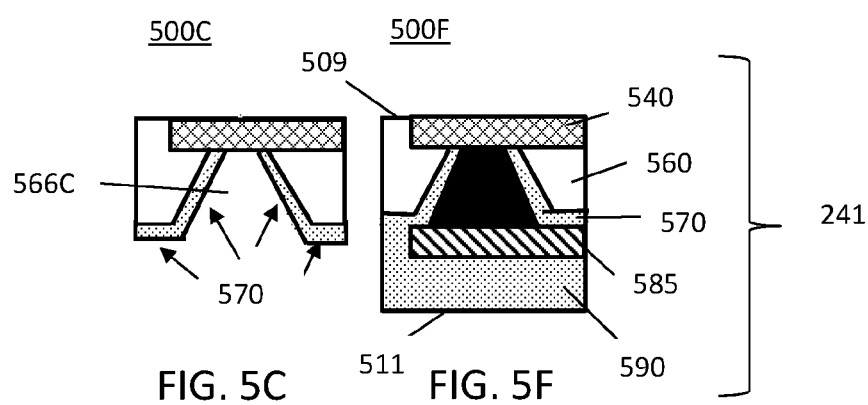

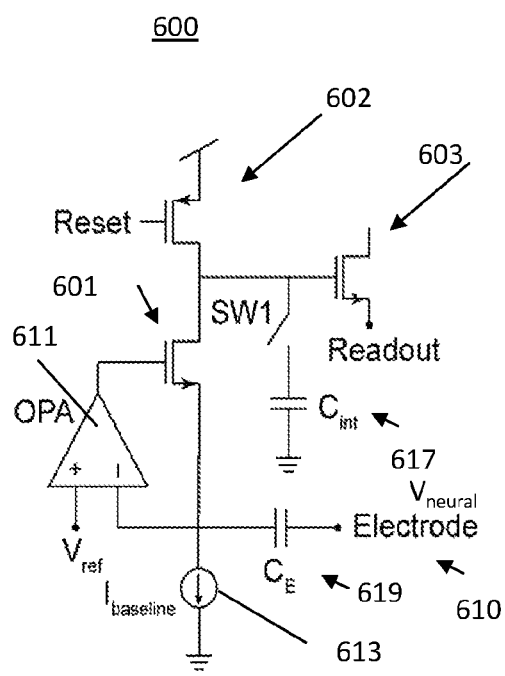 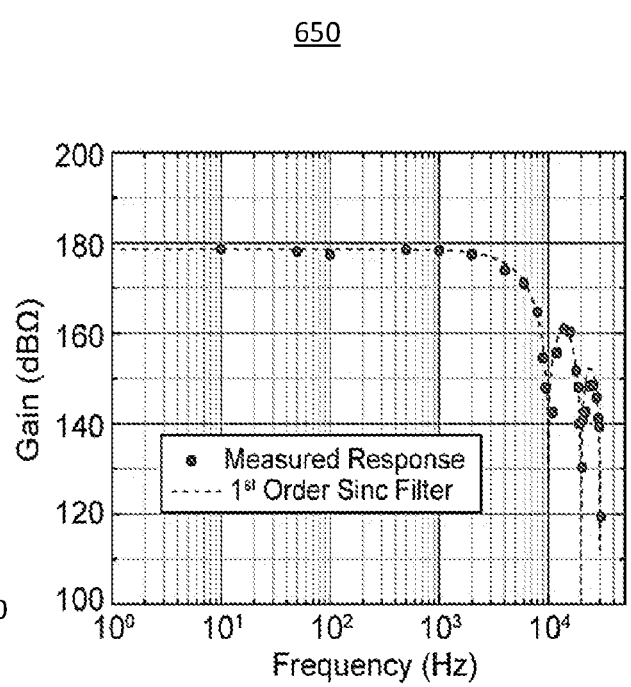
FIG. 6A                                       FIG. 6B 900A  900B  900C 907  917  210  927

FIG. 17A  Sampling  1700A
▲ Delta-modulator
✕ Constant-rate sampling
FIG. 17B  Pulse trains  1700B
FIG. 17C  Reconstruction using delta-modulator  1700C
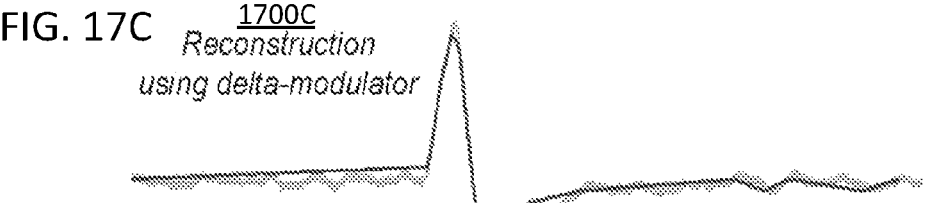
FIG. 17D  Reconstruction using constant-rate  1700D

MONOLITHIC NEURAL INTERFACE SYSTEM

CROSS-REFERENCE TO RELATED APPLICATIONS

This application claims the benefit of U.S. Provisional Application No. 62/588,605, titled "MONOLITHIC NEURAL INTERFACE SYSTEM," filed Nov. 20, 2017, and incorporated herein by reference in its entirety.

FIELD OF THE INVENTION

The present invention relates to a neural interface system and in particular a neural interface system configured as a monolithic system.

BACKGROUND

A device or system that interfaces to the brain is referred to as a brain-machine interface (BMI) or a brain-computer interface (BCI). Such devices provide a direct communication pathway to brain neurons, sensing brain neural signals for brain research and generating and transmitting brain signals to appropriate brain neurons to augment or repair human cognitive or sensory-motor functions.

Invasive BCI's are implanted directly into the grey matter of the brain during neurosurgery. Invasive BCI devices can repair damaged sight and restore movement, or provide new functionality for paralyzed patients, for example by using devices that assist the patient through an interface to a computer or robot arm. Because they are situated in the grey matter, invasive devices produce the highest quality signals among all BCI devices, but are prone to scar-tissue build-up, causing signal attenuation as the body reacts to a foreign object in the brain.

Non-invasive BCI's involve the use of EEG (electroencephalogram) devices that detect electrical activity in the brain. Although EEG-based interfacing devices are easy to wear and do not require surgery, they have relatively poor spatial resolution and cannot effectively use higher-frequency signals because the skull dampens such signals, thereby dispersing and blurring the electromagnetic waves created by the neurons.

Invasive BCI's are implanted inside the skull but outside the brain, either on the dura mater or subdurally. As expected, these devices provide better signal quality than non-invasive BCI's and present a lower risk of forming scar tissue than invasive BCI's. This intermediate BCI modality shows promise due to higher spatial resolution, good signal-to-noise ratio, and useful signals over a wider frequency range.

In addition to the various BCI modalities described above, external equipment (e.g., amplifiers, recorders) is required to monitor and record electrical signals produced by neurons in the brain. Typically, the BCI sensing electrodes are connected to the external equipment by a wired connection. But the wired connection is cumbersome, limits the mobility of the patient, and necessitates the use of transcutaneous wires that present an infection risk.

Each of the described BCI techniques requires an array of sensors for sensing/receiving the neural signals. The parallel neural signals received by such an array (typically disposed within the sensory cortex or the primary motor cortex for an invasive BCI device) encode information that can be used to guide research in restoring cognitive or motor functions. The array can also supply neural signals to brain regions in an effort to restore cognitive and motor functions. The quality of the information derived from the sensor array depends on the density and resolution of the neural signals that are sensed, which is directly related to properties of the sensor array, including the spacing and sensitivity of the array electrodes.

But the electrode density in current brain-machine interface devices remains insufficient to be clinically relevant for many patients; significant improvements are required to help severely disabled patients regain full mobility or resolve other impaired functions. For example, restoring limb movements may require a BMI to monitor 5,000-10,000 neurons simultaneously. Full-body movements may require 100,000 neural measurements.

Fully-implantable neural interface systems are designed with a complex integration of many components including: electrode arrays, amplifiers, processors, wireless transmitters, and a power source. Systems of the prior art use wire feedthroughs to establish electrical connections between the components, and the connections are insulated with materials that prevent leakage.

FIGS. 1A and 1B illustrate current state-of-the-art BCI devices 10A and 10B. These prior art techniques present many limitations: scalability (i.e., adding sensors) is severely limited by space limitations. The device 10A has low scalability in using external wires for electrode-amplifier pairings. The device 10B is represented as an exploded view of a BCI device. The device 10B include a battery 15. The device runtime is limited by battery capacity, wireless signals, such as from wireless transmitter 25, are attenuated and distorted by metal enclosures, long-term durability for non-metallic enclosures, such as polyetheretherketone (PEEK) casing 20, is uncertain, non-hermetic sealing against body fluids is problematic, implant device size complicates surgical procedures and causes discomfort and risks to the patient. The device 10B may include an amplification, multiplex (MUX) and digitization circuitry 30 within a polymer attachment 35 to which a careport pedestal 40 may be attached.

Significant challenges are presented in moving forward to and beyond 1000 sensing/recording electrodes (also referred to as channels since each electrode creates one data channel). These and other issues associated with current BCI devices must be resolved to advance the state-of-the-art and offer disabled patients a path to recovery.

SUMMARY

Embodiments herein relate to a neural interface system and in particular a neural interface system configured as a monolithic system and a method of manufacture. The embodiments also relate to a wireless, battery-less monolithically-integrated neural interface (MINI) device.

An aspect of the embodiments includes a device comprising monolithic substrates forming a chip including a wireless, battery-less monolithically-integrated neural interface (MINI) device configured to be implanted. The chip comprises an integrated circuit (IC) being embedded in a first monolithic substrate and comprising a plurality of amplifiers configured to amplify received neural signals from a monitored subject, and a radio data signal generator configured to process the amplified neural signals and generate a multiplexed digital signal. The chip includes radio-frequency (RF) planar coils embedded in a second monolithic substrate, being electrically connected to the IC through the first monolithic substrate, being configured for wireless transmission of the multiplexed digital signal to a remote wireless device and being configured to receive wireless power signals to power the IC. A plurality of on-chip electrodes is included to directly sense the neural signals of the subject and provide the neural signals to the plurality of amplifiers.

A further aspect of the embodiments includes a system comprising a wireless, battery-less monolithically-integrated neural interface (MINI) device comprising a chip. The chip comprises an integrated circuit (IC) being embedded in a first monolithic substrate and comprising a plurality of amplifiers configured to amplify received neural signals from a monitored subject, and a radio data signal generator configured to process the amplified neural signals and generate a multiplexed digital signal. The chip includes radio-frequency (RF) planar coils embedded in a second monolithic substrate, being electrically connected to the IC through the first monolithic substrate, being configured for wireless transmission of the multiplexed digital signal and being configured to receive wireless power signals to power the IC. The MINI device also includes a plurality of on-chip electrodes configured to directly sense the neural signals of the subject and provide the neural signals to the plurality of amplifiers. The system includes a prosthetic device having coupled thereto a computing device and an external power source and configured to be worn by the subject wherein the computing device receives the multiplexed digital signal and the external power source supplies the wireless power signals to the MINI device.

A still further aspect of the embodiments includes a method comprising manufacturing a chip for a wireless, battery-less monolithically-integrated neural interface (MINI) device. The manufacturing of the chip comprising: embedding an integrated circuit (IC) comprising a plurality of amplifiers configured to amplify received neural signals from a monitored subject in a first monolithic substrate; embedding a radio data signal generator configured to process the amplified neural signals and generate a multiplexed digital signal; and embedding a radio-frequency (RF) planar coils in a second monolithic substrate, being electrically connected to the IC through the first monolithic substrate, being configured for wireless transmission of the multiplexed digital signal to a remote wireless device and being configured to receive wireless power signals to power the IC. The method includes on-chip integrating a plurality of on-chip electrodes on the chip, the plurality of on-chip electrodes configured to directly sense the neural signals of the subject and provide the neural signals to the plurality of amplifiers.

BRIEF DESCRIPTION OF THE FIGURES

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIGS. 1A and 1B illustrate current state-of-the-art BCI devices;

FIGS. 3A-3D illustrates steps associated with unguided-electrodeposition of an on-chip gold electrode for an on-chip pillar electrode array in the MINI device;

FIG. 5A-5F illustrate steps for backplane integration of an RF planar coil of the MINI device using through-silicon via (TSV);

FIG. 6A illustrates a neural recording circuit with an intrinsic sinc filter;

FIG. 6B illustrates a graphical representation of the intrinsic filter of attenuating high frequency which contributes to aliasing noise;

FIG. 17A illustrates a neural signal sampling using the delta-modulator and traditional neural recording system wherein the spike is an example of 1-mV neural spike, triangles (▲) indicate where the delta-modulator will sample, and crosses (x) show where the traditional system will sample;

FIG. 17B illustrates the pulse trains based on sampling the neural signal based on the delta-modulator's samples;

FIG. 17C illustrates the reconstruction of the neural signal based on the delta-modulator's samples;

FIG. 17D illustrates the reconstruction based on the constant-rate sampling;

DETAILED DESCRIPTION

Figure 2A:
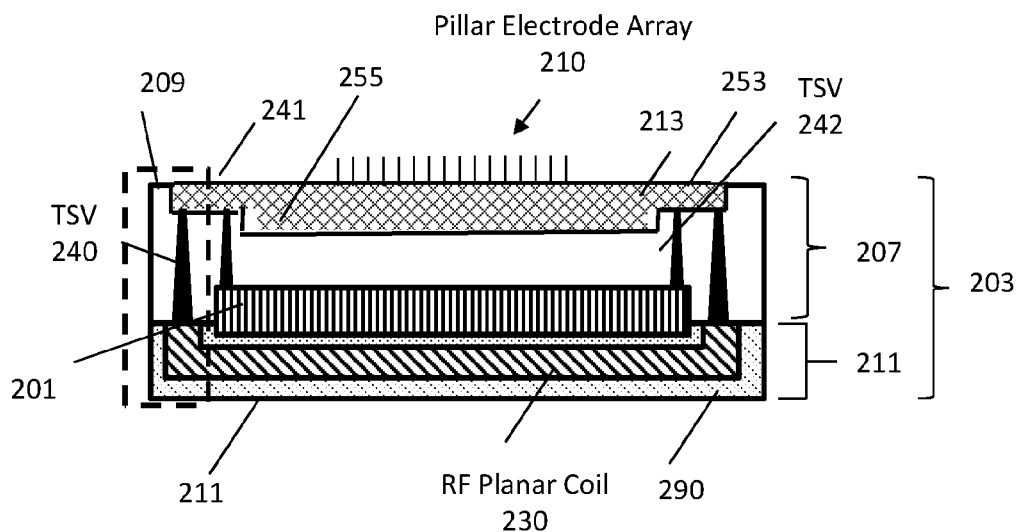
FIG. 2A illustrates a cross-sectional view of a monolithically-integrated neural interface (MINI) device.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Thus, the development of a new brain-machine interface with large-scale recording capability is needed to advance basic brain research, large-scale brain mapping, and clinical translation of brain-machine interface devices into a product suitable for patient use.

Disclosed herein is a wireless neural interface (a BCI or BMI) apparatus that integrates the wireless, battery-less neural system onto a thin substrate, e.g., a silicon substrate in one embodiment. Due to the monolithic form of the device, no wires to external devices or complex packaging techniques are required. Also, the wireless, battery-less neural interface apparatus embodiments offer a significantly lower manufacturing cost by using conventional semiconductor fabrication methods. The embodiments are related to a monolithic integration of neural interface system on a silicon die which is a scalable neural interface.

The system includes an integrated planar electrode array, a radio frequency (RF) planar coil on a separate silicon die, and a complementary metal-oxide semiconductor (CMOS) 1000-channel amplifier array that uses an off-chip telemetry link capability. In some embodiments, the RF planar coils and capacitors are monolithically integrated on the same silicon die. By way of non-limiting example, the embodiments may include a fully integrated BMI system on a single 0.04-cm$^3$ silicon die.

Rich information from the sensory cortex can only be extracted with a set of high-density recordings. The monolithic integration of every component into a single silicon die enables high-density recordings by eliminating external wires and linking all the electronic interconnections through CMOS interconnects.

Monolithic integration of all components that establish all electronic connections internally. This eliminates the wire feedthrough and packaging.

The quality of information that can be acquired/stimulated depends on the size/pitch of the electrode array. The current state-of-the-art is limited to 100 s of electrical recordings. By building the electrode directly on top of the amplifier, the system integrates over 1000 channels (1000-ch) for neural recording. This method lays the groundwork for the development of higher throughput.

The system may be completely battery-less. The integrated RF planar coils receive power (~10 mW at 2.64 MHz) and transmit data through RF coupling. The low-frequency power transmission prevents tissue damage.

Although the embodiments disclosed herein describe the wireless monolithically-integrated neural interface (MINI) device primarily in the context of sensing neural signals, those skilled in the art recognize that the neural monolithic interface of the MINI device described by the disclosed teachings can also be advantageously used to generate neural signals and supply those signals to brain tissue (either directly or through the skull or through the dura) and thereby stimulate cognitive and motor-sensory functions. Incidentally and advantageously, when the MINI device is incorporated into a neural prosthetic device, the neural monolithic interface may result in lower prices and improved performance for neural prosthetics devices. The system may provide a neural interface implant for use by paralyzed patients in need of assistive prosthesis, for example.

One embodiment discloses a monolithically integrated 1000-channel neural interface system into a single integrated circuit (IC) fabricated on a silicon substrate for simultaneous recording capability. Integration of most of the components into a single IC enables high-density sensing and recording of the neural signals. The electronic components are also fabricated on the IC and linked by sub-micron electrical interconnections. This approach yields advantages, compared to the conventional approach, including design simplicity, elimination of external wiring, and reduction of packaging complexity.

As defined herein neural signals include the nerve impulse which corresponds to neurons communicating with each other. The neural signal comprises electrical signals propagating through the neuron in the form of action potentials and local field potentials. This electrical signal is generally referred to as the neural signal being sensed or detected by electrodes of the MINI device described herein. The neurons may comprise on or more of motor neurons, sensory neurons and interneurons.

The recorded signals, by the MINI device, are converted to digital signals in an analog-to-digital converter (the digital data stream may be compressed in certain embodiments) and then wirelessly transmitted to a processing station for analysis and recording.

The embodiments described herein provide several desirable features: (1) on-chip integration of a pillar electrode array; (2) backplane integration of RF (radio frequency) planar coils and capacitors, and (3) a low-power small-footprint amplifier array and peripheral circuits for high-throughput of neural signals and recording of those signals. FIGS. 2B and 2C illustrate the frontplane and backplane of the MINI device and, in FIG. 2A a cross-section through the MINI device, illustrating the various device layers and interconnections.

Figure 2B:
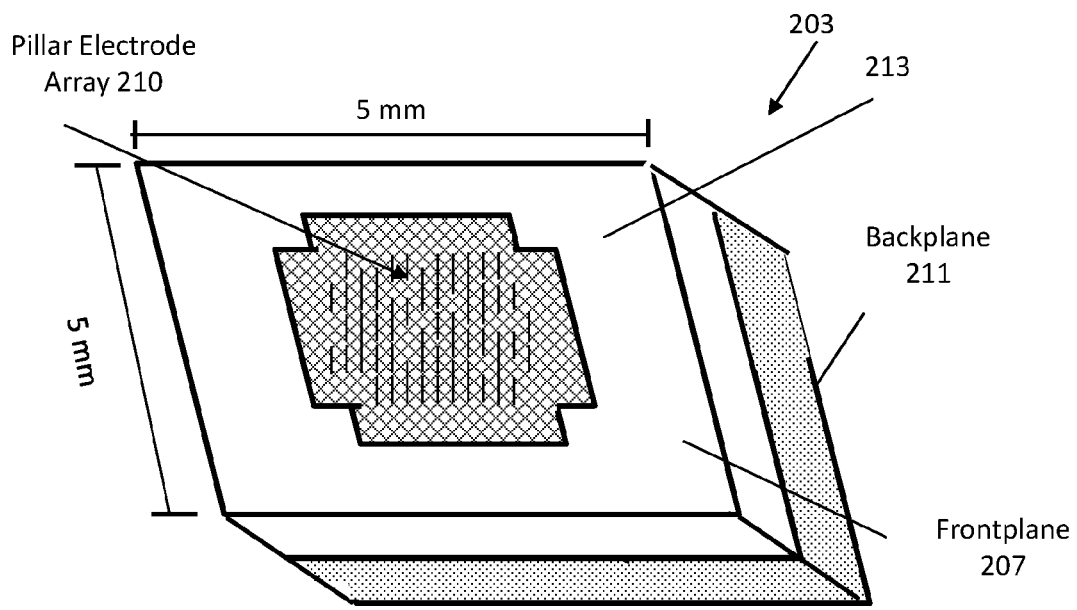
FIG. 2B illustrates a perspective view of a frontplane of the MINI device of FIG. 2A.
Figure 2C:
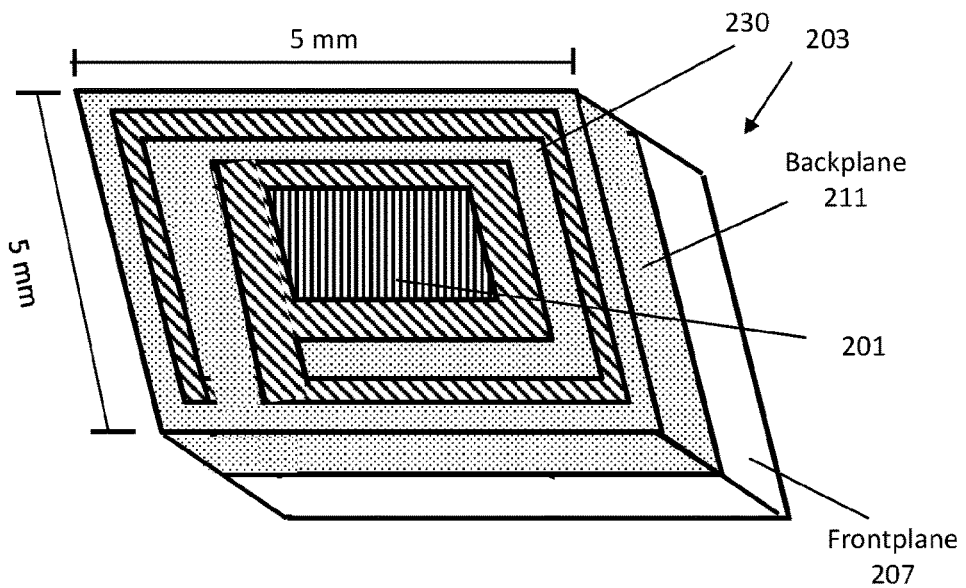
FIG. 2C illustrates a perspective view of a backplane of the MINI device of FIG. 2A.

FIG. 2A illustrates a cross-sectional view of a monolithically-integrated neural interface (MINI) device 200A. The MINI device 200A includes a frontplane layer 207 and a backplane layer 211, collectively referred sometimes as the chip 203. The frontplane layer 207 and backplane layer 211 are generally monolithically integrated to form chip 203 into a single MINI device 200A. The RF planar coil 230 is denoted with diagonal hatching. The frontplane layer 207 includes an external surface 209. The backplane layer 211 includes an external surface 213 wherein surface 209 and surface 213 are generally top and bottom layers. The terms top and bottom are not meant to be limiting but are used as a frame of reference. Top and bottom may be first and second.

Referring also to FIG. 2C, a perspective view of a backplane layer 211 of the MINI device of FIG. 2A is illustrated. The backplane layer 211 of the MINI device 200A may include a passivation layer 290, represented as dotted hatching. The passivation layer 290 being protective material or shell to protect against corrosion, for example. The backplane layer 211 includes an RF planar coil 230, denoted by diagonal hatching, formed by applying, for example, an aluminum pattern in the form of a coil, as best seen in FIG. 2C. The aluminum pattern is integrated into the backplane layer 211 such that the aluminum pattern is generally exposed to the exterior so that radio frequency (RF) signals may be received or transmitted, as will be discussed in more detail in relation to FIG. 2D.

Opposite ends of the RF planar coil 230 are interfaced with through-silicon vias (TSVs) 240, represented as solid black, wherein the TSV 240 is integrated into the frontplane layer 207, as described in relation to FIGS. 5A-5F. The bottom end or widest end of the TSV 240, which comprises a metal is attached or bonded directly to portions of the RF planar coil 230. By way of non-limiting example, the metal of the TSV 240 may include copper (Cu). Generally, the bottom end of the TSV 240 is attached to an interior surface of the RF planar coil 230 wherein the exterior surface of the RF planar coil 230 is exposed for transmissions. Specifically, RF planar coil 230 may form a generally U-shape. The U-shape includes two legs. Each leg has a width which is at least the length of the bottom side of the TSV 240. Each leg has coupled thereto a TSV 240, each of which extends to the IC 213, denoted as cross hatching.

Figure 2D:
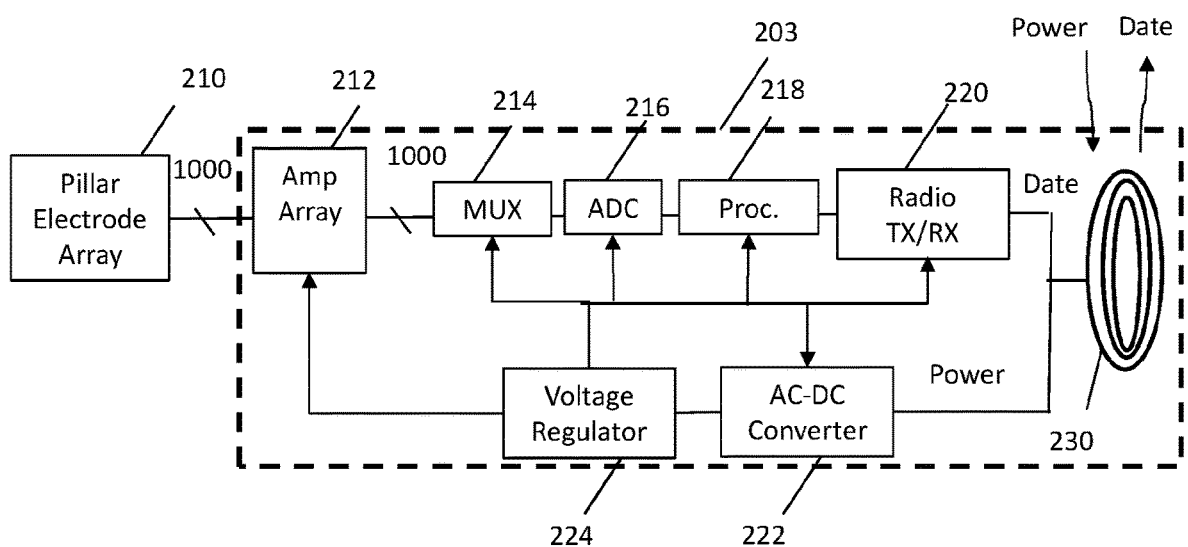
FIG. 2D illustrates a block diagram of a MINI device according to an embodiment.

FIG. 2B illustrates a perspective view of a frontplane layer 207 of the MINI device of FIG. 2A. The frontplane layer 207 includes the integrated circuit layer 213, as will be discussed in more detail in relation to FIG. 2D. The TSV 240 is truncated at the integrated circuit (IC) 213. The frontplane layer 207 includes a top or external surface 209 having formed in a portion thereof IC layer 213, represented as cross hatching. The IC layer 213 has a first layer portion 253 and a second layer portion 255. The first layer portion 253 has the TSV 240 directly coupled thereto which connects the RF planar coil 230 to the RF (radio) transceiver (TX/RX) 220 (FIG. 2D). The second layer portion 255 below the second layer portion 255 is generally narrower than the first layer portion 253 and forms a shoulder or step up to the first layer portion 253.

The backplane layer 211 further comprises a capacitor layer 201 represented with vertical hatching. The length of the capacitor layer 201 is less than the length of the first layer portion 253 and longer than the second layer portion 255. The distal ends of the capacitor layer 201 has directly coupled thereto a second set of TSVs 242. The TSV 242 is generally the same as the TSV 240. The set of TSVs 242 may be generally coupled to the first (top) layer portion 253 on opposite sides of the second (bottom) layer portion 255.

The top of the IC layer 213 has integrated thereto a pillar electrode array 210. Each electrode of the array 210 corresponds to a different channel. The MINI device 200A may have 1000 or more electrodes.

The MINI device 200A is fabricated according to the following steps: fabrication of the integrated circuit according to a complementary metal-oxide-semiconductor (CMOS) process; post-CMOS processing to form the pillar electrode array on the chip; etching the substrate (or employing substrate grinding/polishing techniques) to reduce substrate thickness to about 50 μm (in one embodiment) to improve substrate flexibility; patterning capacitors and radio-frequency (RF) planar coils on a backplane of the substrate; creating a low-leakage barrier by surrounding the die with an insulating material (e.g., $SiO_2/Si_3N_4/SiC$) compatible with CMOS technology and materials processing. SiC is silicon carbide. $SiO_2$ is silicon dioxide. $Si_3N_4$ is silicon nitride.

By the monolithic integration of every device component, the use of external wiring is eliminated as all component connections are made within the integrated circuit and connections to ancillary external equipment is made over a radio frequency link. In the absence of exposed wires and connections that are susceptible to corrosion by bodily fluid, integration of the array and the processing components eliminates conventional packaging requirements for an implanted neuro sensor array. By forming interconnections between the array and the device components on the chip, the device can easily accommodate 1000 (or more) electrodes.

FIG. 5A-5F illustrate steps for integration of the backplane of an RF planar coil of the MINI device using through-silicon via (TSV) as represented in dashed block 241 in FIG. 2A. The steps of FIGS. 5A-5F are represented in cross-sectional views of the steps 500A, 500B, 500C, 500D, 500E, and 500F forming that portion in dashed block 241 in FIG. 2A. The integration of the backplane of RF planar coil uses through-silicon vias 240 (FIG. 2A). Like layers of the RF planar coil have the same hatching in each different step. Thus, the reference number per layer will be generally used once in FIGS. 5A-5E. Additionally, the hatching of layers in block 241 of FIG. 2A matches the hatching of FIGS. 5A-5F.

At FIG. 5A, the step 500A for integration of the backplane may include forming a first material layer 560 suitable for monolithic integration which represents the frontplane layer 507. By way of non-limiting example, the first material layer 560 may include silicon (Si). The first material layer 560, represented without hatching, includes frontplane layer 507 and a bottom side 562B. A portion of the frontplane 507 has formed thereon an integrated circuit 540 of components, represented as cross hatching, of the MINI device 200A.

At FIG. 5B, the step 500B for integration of the backplane may include KOH etching in the first material layer 560 to form a via cavity 566B. The via cavity 566B has a generally truncated triangularly-shape, along a cross-sectional view and is bounded by the first material layer 560. A photoresist (PR) layer 564A, represented with square hatching, is formed on a first side of the via cavity 566B. Likewise, a PR layer 564B is formed on the opposite side of the via cavity 566B.

At FIG. 5C, the step 500C for integration of backplane may include oxidizing the remaining portion of the bottom side 562B of the first material layer 560 to form, for example, an oxide layer 570, represented as dotted hatching. The oxide layer 570 may include silicon dioxide ($SiO_2$). The oxide layer 570 is formed along the surfaces of the remaining bottom side 562 on opposite sides of the via cavity 566B and the walls of via cavity 566B to form via cavity 566C. Oxidation of silicon may include thermal oxidation to form a thin oxide layer 570 while maintaining a generally truncated triangular shape of via cavity 566C.

At FIG. 5D, the step 500D for integration of backplane may include copper (Cu) electrodeposition within the via cavity 566C (FIG. 5C). The cavity 566C is filled with an amount of copper (Cu) such that the copper fills the empty space of cavity 566C to and between the oxide layers 570 to form a TSV 575 (i.e., via 240) also represented with a solid black fill. The cavity 566C may be filled such that the bottom side 576 of the TSV 575 is essentially flush with the oxide layer 570.

At FIG. 5E, the step 500E for integration of the backplane may include forming an aluminum pattern 585, represented as diagonally hatched, to extend along the entire length of the bottom side 576 of the TSV 575 and one side of the oxide layer 570. By way of non-limiting example, the aluminum pattern 585 may include a RF coil pattern 585 to form the RF coil (i.e., RF coil 230 FIG. 2C).

At FIG. 5F, the step 500F for integration of the backplane may include applying a passivation layer 590 over the remaining oxide layer 570 formed over the first material layer 560. The RF coil pattern 585 may remain exposed to permit transmission of data and reception of power. The passivation layer 590 is also represented as dotted hatching. The thickness of the passivation layer 590 may form the backplane layer 509 having an outer backplane surface 511.

The RF coil has been simulated or modeled and achieves approximately 16.5-mW power transmission.

Also, integration of the capacitors and RF planar coils (used for data transfer and power generation as described below) on the backplane (or front plane) of the substrate provides for battery-less operation by simultaneous wireless power (at approximately 10 mW) and data transmission. Power is transferred using a wireless induction charging technique whereby an electromagnetic field transfers energy from an external power source to one of the RF planar coils. The capacitors and coils are fabricated using conventional CMOS processes and connected to other circuit elements within the integrated circuit using through-silicon conductive vias.

In an embodiment with two RF coils, a first coil provides data transmission over an RF link and a second coil generates power responsive to an external power source coupled to the second coil via an RF link.

The data is transmitted from the first RF coil at a frequency of about 900 MHz according to the OOK (on-off keying) modulation scheme, which is very power efficient compared to other digital modulation schemes for data transmission protocols.

In one embodiment, about 10 mW of power is supplied at a resonant frequency of 2.64 MHz (or in any case less than 3 MHz) by RF coupling of an electromagnetic field generated by the external power source. This power level is below RF safety guidelines as promulgated by the Federal Communications Commission (FCC). Those safety guidelines limit the power level to 100 $mW/cm^2$ as projected onto a patient or subject. Also, to minimize radiation-induced tissue damage, a low-frequency power-transmitting signal is used, as it is known that water is a poor absorber of such low frequency signals.

Table 1 below sets forth an approximate power consumption range for each component within the neural interface device.

| Integrated Components | Anticipated Range of Power Consumption |
|---|---|
| Amplifier array (200-1000 nW/ch) | 0.2-1 mW |
| 12-bit analog-to-digital converter | 0.4-2 mW |
| Digital processor | 0.4-2 mW |
| OOK Telemetry unit | 0.25-5 mW |
| Total MINI system | ≤10 mW |

The RF power signal from the external power source 880 (FIG. 8A-8B) generates an AC signal in the second coil. Close coupling of the second coil and the silicon substrate may create a parasitic capacitance that attenuates power transmission, thus the second coil is disposed in a back plane of the device.

Power transmission efficiency is optimized at a separation distance of about 1.5 cm between the second coil and the external power source. After converting to direct current (DC), the resulting signal is filtered, and an output voltage is set by a voltage regulator.

A sizable capacitor is required for filtering the converted DC signal. To achieve a capacitance as large a 1 μF for proper filtering and subsequent voltage regulation, a metal-insulator-metal (MiM) capacitor occupying an area of about 25 $mm^2$ is disposed on the backplane of the substrate.

The power transmission coil and the capacitor are disposed in different layers of the substrate separated by a passivation layer to avoid interference effects, as best seen in FIG. 2A.

In another embodiment, a battery can be incorporated into the monolithic device, thereby eliminating the RF power coupling to supply real-time power to the components of the device. Preferably, the RF power coupling would be used to charge the battery.

In another embodiment, especially advantageous for increasing power transmission, a silicon-on-insulator (SOI) substrate is used, in lieu of a silicon substrate. This embodiment increases the distance between the silicon bulk and the planar coils thereby lowering the parasitic capacitance.

In yet another embodiment the substrate size is increased beyond 25 $mm^2$ to allow for increasing the inductance and quality factor of the coils, while reducing the coil series resistance. A larger substrate also permits fabrication of a larger coil. In any case, the MINI device may remain below the size of current state-of-the-art BCI systems, which are about 68.64 $cm^3$ in size with about 100 electrodes in the array.

The thin substrate provides a MINI device volume of about 0.0125 cm³, which is substantially smaller than current state-of-the-art devices, i.e., 68.64 cm³. The 50-μm thickness offers substrate flexibility for implantation under the skull. Also, having all components integrated onto the chip simplifies the surgical implant procedure.

FIGS. 3A-3D illustrates steps associated with unguided-electrodeposition of an on-chip gold electrode for an on-chip pillar electrode array in a MINI device. In FIG. 3A, the step for unguided electrodeposition to from an on-ship gold electrode includes the step 300A where an opening 315A is formed in the aluminum (Al) layer overlaid on the CMOS die 305A. A pillar 310A is shown raised above the CMOS die 305A and used for the on-chip integration of the electrodes. In FIG. 3B, the step 300B includes etching the Al in section 315B through the pad 310B on CMOS die 305B. In FIG. 3C, at step 300C, the pad section 310C is plated with nickel 315C through electrodeposition. The nickel does not extend to CMOS die 305C. In FIG. 3D, at step 300D, gold 315D is electroplated in section 310D over the nickel layer. The gold plating does not extend to CMOS die 305D.

The on-chip electrode array 210 (FIG. 2A) is formed using electrodeposition techniques. Because electrodeposition is an isotropic deposition process, the high-aspect ratio pillar electrodes are fabricated by guiding the electrodeposition process with a patterned photoresist (PR) layer.

Figure 4A:
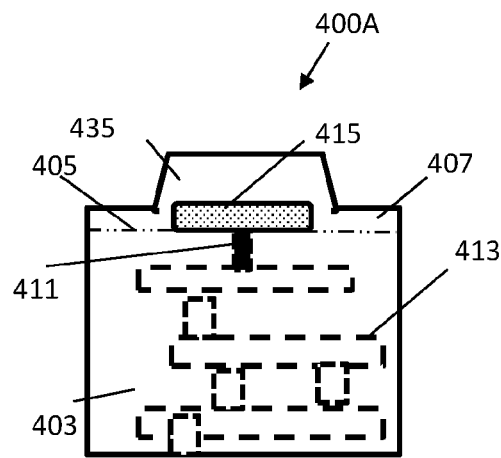
FIGS. 4A-4F illustrates step-by-step diagrams of guided-electrodeposition to fabricate a pillar electrode with a tungsten core.
Figure 4B:
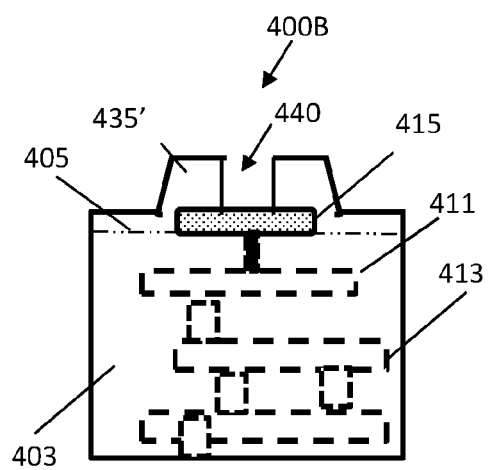
Figure 4C:
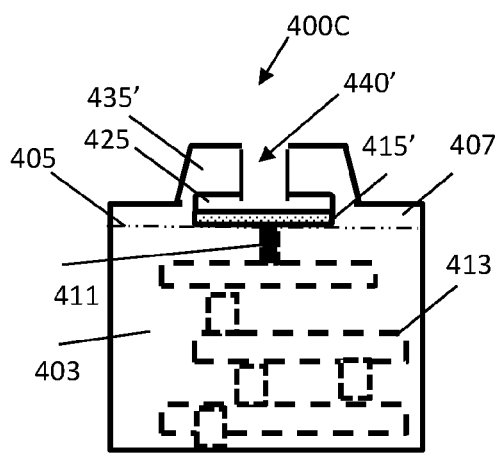
Figure 4D:
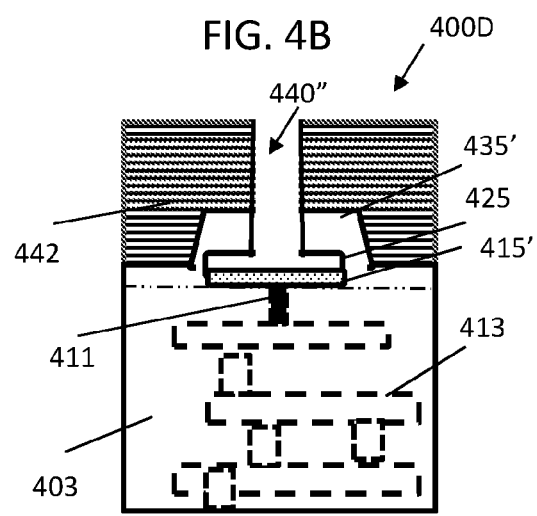
Figure 4E:
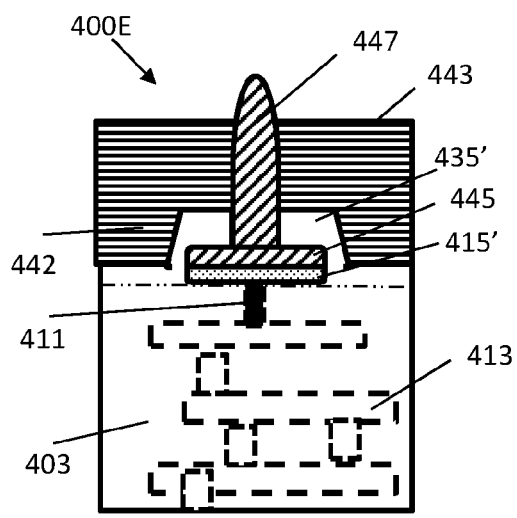
Figure 4F:
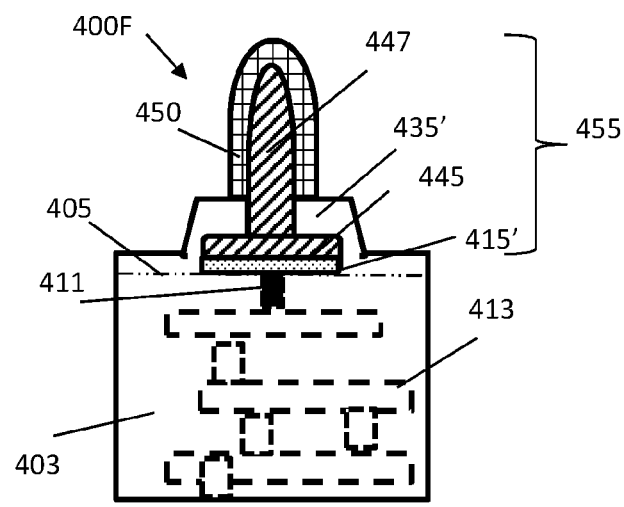

FIGS. 4A-4F illustrates step-by-step diagrams 400A, 400B, 400C, 400D, 400E and 400F of guided-electrodeposition to fabricate a pillar electrode 455 with a tungsten core, as best seen in FIG. 4F. Like components will have the same reference numeral. However, if the component is changed the reference number will include a prime or double prime indicator. Because FIGS. 4A-4F has similar reference numerals, while once a reference numeral is mentioned in one figure, it may not be referenced again unless necessary when describing a subsequent figure. One desirable property of the pillar electrode array is a high structural resistance to shear stress caused by the surface of the brain, both during the surgical procedure and after implantation. Thus, each pillar must exhibit a high Young's modulus, in some embodiments. In one embodiment, each electrode comprises a tungsten core and a gold external surface, yielding a relatively stiff pillar and electrode. Embodiments of the array 210 comprise different shapes and lengths depending on the implantation site. Preferably, each pillar is at least a 50-μm long to penetrate the human dura or pia.

In FIG. 4A, the step 400A will be described in relation to the formation of the CMOS die 403 having embedded or integrated therein an integrated circuit (IC) 413 such as described in relation to FIGS. 2A and 2D. The IC 413 is represented in layers of dashed-line boxes for illustrative purposes. The CMOS die 403 may be made of silicone, for example. A conductive lead 411 is embedded in the CMOS die 403 and coupled to the IC 413. Other leads may be provided.

The CMOS die 403 has embedded on a top side thereof an aluminum (AL) pad 415 or strip, represented with dotted hatching, being electrically coupled to the conductive lead 411. The conductive lead 411 being below the Al pad 415. The Al pad 415 or strip has a first height and width. The AL pad 415 is above the plane of the top surface 405, represented as a dash dot, dot line, of the CMOS die 403 and embedded directly under a pillar 345. The pillar 345 is formed by an oxide layer 407, for example made of silicon dioxide ($SiO_2$), applied over the top surface 405 of the CMOS die 403 and the top of the Al pad 415. Since, the AL pad 415 is above the top surface of the CMOS die 403, a raised portion is formed which is denoted as the pillar 345.

In FIG. 4B, the step 400B includes etching the oxide layer 407 such that pillar 345' has formed therein an open channel 440 or pathway extending down to a top surface of the Al pad 415. In FIG. 4C, the step 400C includes etching the Al pad 415' through the open channel 440' such that material of the Al pad 415' is removed out through the channel 440' of the pillar 435' to reduce the Al pad 415' by an amount and simultaneously form an electrode support-base (ESB) cavity 425. The ESB cavity 425 may be the same width as the Al pad 415. The width of the ESB cavity 425 should be larger than the width of the open channel 440'.

In FIG. 4D, the step 400D includes creating a patterned photoresist (PR) layer 442, represented with horizontal hatching, above the oxide layer 407 and corresponding pillar 435'. The height of the photoresist layer 442 is a function of the height needed for the electrode. The PR layer 442 has an open channel 440". Thus, an open channel which includes both the open channel 440' formed in the pillar 435' down to the etched AL pad 415' and the open channel 440" in the PR layer 442 such that a clear pathway is formed down to the ESB cavity 425. In some embodiments, the open channel 440' and open channel 440" may include the same diameter except in the ESB cavity 425.

In FIG. 4E, the step 400E includes forming an electrode conductive core base 445, represented with diagonally hatching, within the ESB cavity 425 and forming a conductive electrode core 447 along the remaining length of the open channel 440' and length of open channel 400", also represented with diagonally hatching. The step 400E may include electroplating the ESB cavity 425 and the open channels 440' and 440" with a conductive metal to fill both the cavity 425 and channels 400' and 400" to form a solid unitary electrode core structure which may include the electrode core 447 supported by an integrated electrode base 445. In some embodiments, the electroplating may include extending the length of the electrode core 447 above a top surface 443 of the PR layer 442. In some embodiments, the conductive metal includes tungsten or other structurally strong material.

In FIG. 4F, the step 400F includes removing the PR layer 442 and subsequently encapsulating and completely surrounding the conductive electrode core 447 extending above the pillar 435' with a gold (Au) layer 450, denoted with square hatching. The gold layer 450 extends down to the pillar 435'. The gold layer 450 also encapsulates the tip of the conductive electrode core 447. The conductive electrode 455 includes the gold layer 450, the conductive electrode core 447 and electrode base 445 in electrical communication with conductive lead 411 in the CMOS die 403.

By way of non-limiting example, the gold layer 450 is electroplated on and around the exposed perimeter surfaces of the electrode core 447.

In another embodiment the pillar-structures array is replaced with a planar electrode array. A device using this this latter array must be implanted subdurally, instead of over the dura mater as is the case for the pillar structures, as the planar array electrodes cannot penetrate the thick membrane of the dura.

FIG. 2D also shows a system block diagram, depicting the principal components of the MINI device 200D. The signals from each electrode in the electrode array 210 are amplified by an associated amplifier in an amplifier array 212 with a one-to-one correspondence, in some embodiments. The multiple electrode signals are multiplexed (such as using a time-division multiple access (TDMA) approach at 10

MS/s) using a multiplexer (MUX) 214 and converted to digital form in and analog-to-digital converter (ADC) 216 at 120 Mbits/s, for example. The digital signals are processed in a processor 218 for data compression, for example. The processor 218 may be a digital signal processor. The signals from processor 218 may be supplied to a radio frequency (RF) transceiver (TX/RX) 220 for creating an RF signal for wireless transmission off-chip through coil 230 to a signal analysis device for recording and analysis, at a remote location.

TDMA multiplexing staggers all integration periods so that, while the data from one amplifier is being read, all other amplifiers continue to integrate the sensed information. This multiplexing scheme may maximize the signal-to-noise ratio (SNR) and minimizes circuit complexity.

As also shown in FIG. 2D, power is supplied via an RF link to the MINI device 200D, converted to direct current (DC) by an AC-DC converter 222, regulated to the proper voltage by a voltage regulator 224, and then supplied to the device components. AC refers to alternating current.

Various amplifier configurations can be used in the monolithic neural sensor of the present invention. According to one embodiment, the MINI device 200D comprises one low-noise amplifier (LNA) of array 212 for each electrode of array 210. Generally, this is a more power-efficient design, but requires a larger area to accommodate the amplifiers. In one embodiment, a 1000-amplifier array 210 occupies an area of about 10 mm$^2$ with a noise level of about 5 $\mu V_{RMS}$ at a sampling rate of 10 kS/s (kilosamples/second). Because the design is scalable, more than 1000 channels, 1000 amplifiers and 1000 electrodes are possible.

FIG. 6A illustrates a neural recording circuit 600 with an intrinsic sinc filter. The amplifiers within the device provide intrinsic rejection of aliasing noise using a sinc filter based on the integration period; this filtering improves the overall signal-to-noise ratio (SNR). This amplifier uses a potentiostat with an integrating capacitor $C_{int}$ 617. The potential generated by neural activity ($V_{neural}$) at the electrode 610 causes a potential drop across capacitor $C_E$ 619 and the resulting current integrates at capacitor $C_{int}$ 617, which is then periodically displayed as a voltage ($V_{readout}$) at the source of transistor 603. A current source 613 provides a current ($I_{baseline}$) which is coupled to a source of transistor 601. The drain of transistors 601 and 602 are coupled together and tied to the gate of transistor 603. Switch SW1 is coupled in the path to capacitor $C_{int}$ 617 and the path between the drains of transistors 601 and 602 and the gate of transistor 603. The switch SW1 opens and closes the path to capacitor $C_{int}$ 617.

The transistor 601 has its gate coupled to an operational amplifier (OPA) 611 receiving inputs $V_{ref}$ and $I_{baseline}$. The electrode 610 is also coupled through capacitor $C_E$ 619 to an input of amplifier (OPA) 611.

The displayed voltage represents $V_{neural}$ as can be seen in the following formula:

$$\Delta V_{readout} = \frac{sC_E \times t_{int} \times (V_{neural} - V_{ref})}{C_{int}}.$$

A high-frequency sine wave is applied to $V_{ref}$ to effectively "re-sample" $V_{neural}$ at the sine wave frequency. At that frequency, the impedance of input capacitor ($sC_E$) is a constant, thus, removing the frequency-dependency of the voltage gain:

$$\text{gain} = \frac{\Delta V_{readout}}{V_{neural} - V_{ref}} = \frac{s_{carrier} \times C_E \times t_{int}}{C_{int}}.$$

In one embodiment the voltage gain is adjusted to 100 by setting the gain parameters to $s_{carrier}=2\times\pi\times5$ kHz, $C_E=2$ pF, $C_{int}=63$ fF, and $t_{int}=100$ μs. The noise level is about 5 $\mu V_{RMS}$ or lower at the sampling rate of 10 kS/s with a 100×100 μm$^2$ size. Thus, in one embodiment the amplifier array is 3.2×3.2 mm$^2$, excluding peripheral circuits such as timing and multiplexer circuits.

According to another embodiment, the amplifier comprises a capacitor feedback amplifier to cancel out the frequency component in the voltage gain. Such amplifiers are well known in the art.

FIG. 6B illustrates a graphical representation 650 of the intrinsic filter of attenuating high frequency which contributes to aliasing noise. The intrinsic filter of integrating system attenuates high frequency which contributes to aliasing noise. The cut-off frequency is ~4.4 kHz at 10 kS/s, as expected by sinc filter.

Figure 7A:
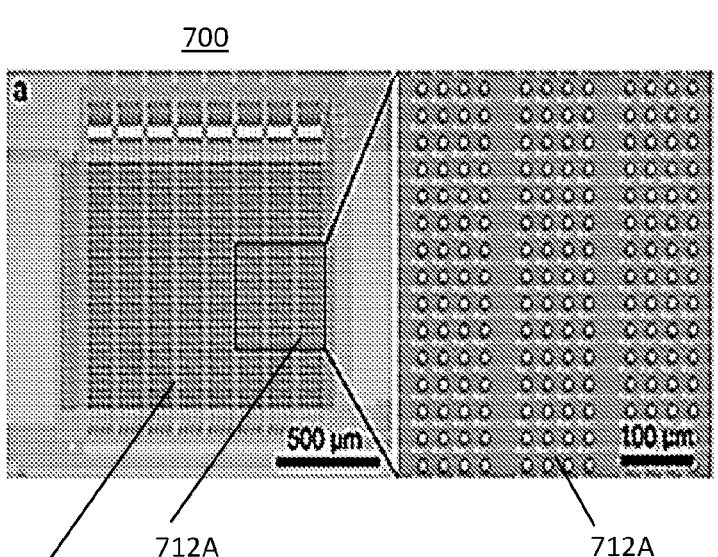
FIG. 7A illustrates a 1000-channel amplifier array and part of the neural recording circuit.

FIG. 7A illustrates a 1000-ch amplifier array 712 and part of the neural recording circuit 700. In FIG. 7A, each amplifier of the 1000-ch amplifier array 712 may be a picoampere amplifier for use in neural recordings via the electrodes. A portion 712A of the amplifier array 712 is expanded.

Figure 7B:
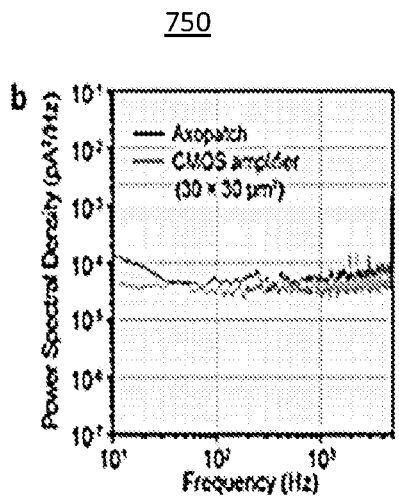
FIG. 7B illustrates a graphical representation of a noise spectral density of the designed complementary metal-oxide semiconductor (CMOS) amplifier array of FIG. 7A compared to the state-of-the-art electrophysiology amplifiers, Axopatch 200B.

FIG. 7B illustrates a graphical representation 750 of a noise spectral density of the designed CMOS amplifier of FIG. 7A compared to the state-of-the-art electrophysiology amplifier, Axopatch 200B.

Figure 8A:
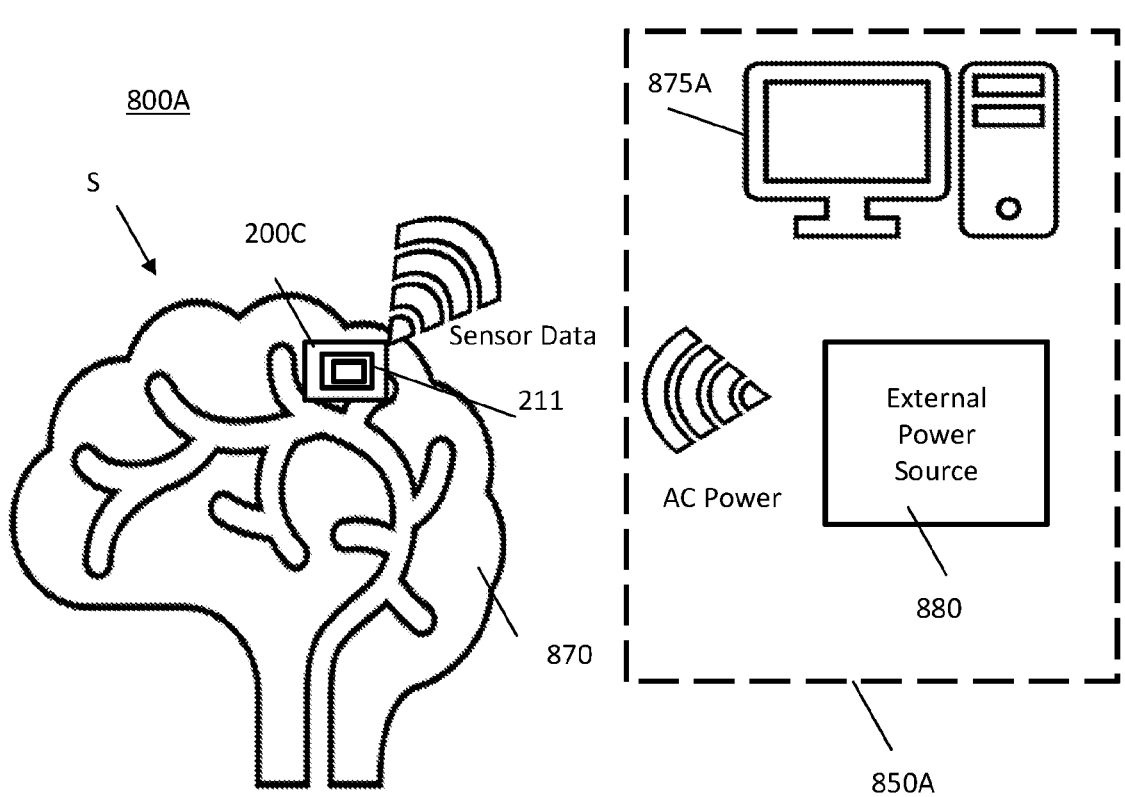
FIG. 8A illustrates a first MINI system.

FIG. 8A illustrates a first MINI system 800A. The MINI system 800A includes MINI device 200C with the backplane 211 shown and a remote system 850A. The MINI device 200C is shown implanted into a subject S at brain 870. The MINI device 200C is configured to communicate with a remote analyzer 875A, such as a computer system as described in relation to FIG. 19. The external power source 880 is configured to provide power signals to the MINI device 200C. The remote system 850A may include the remote analyzer 875A and external power source 880. The remote system 850A may be one device or two separate devices. The distance between the remote system 850A and the MINI device 200C may be limited by the range of wireless communications of the data signals and the power signals. Communications in some embodiments uses telemetry. The system 800A may be used to develop model data from a subject S having the MINI device 200C implanted, for example.

Figure 8B:
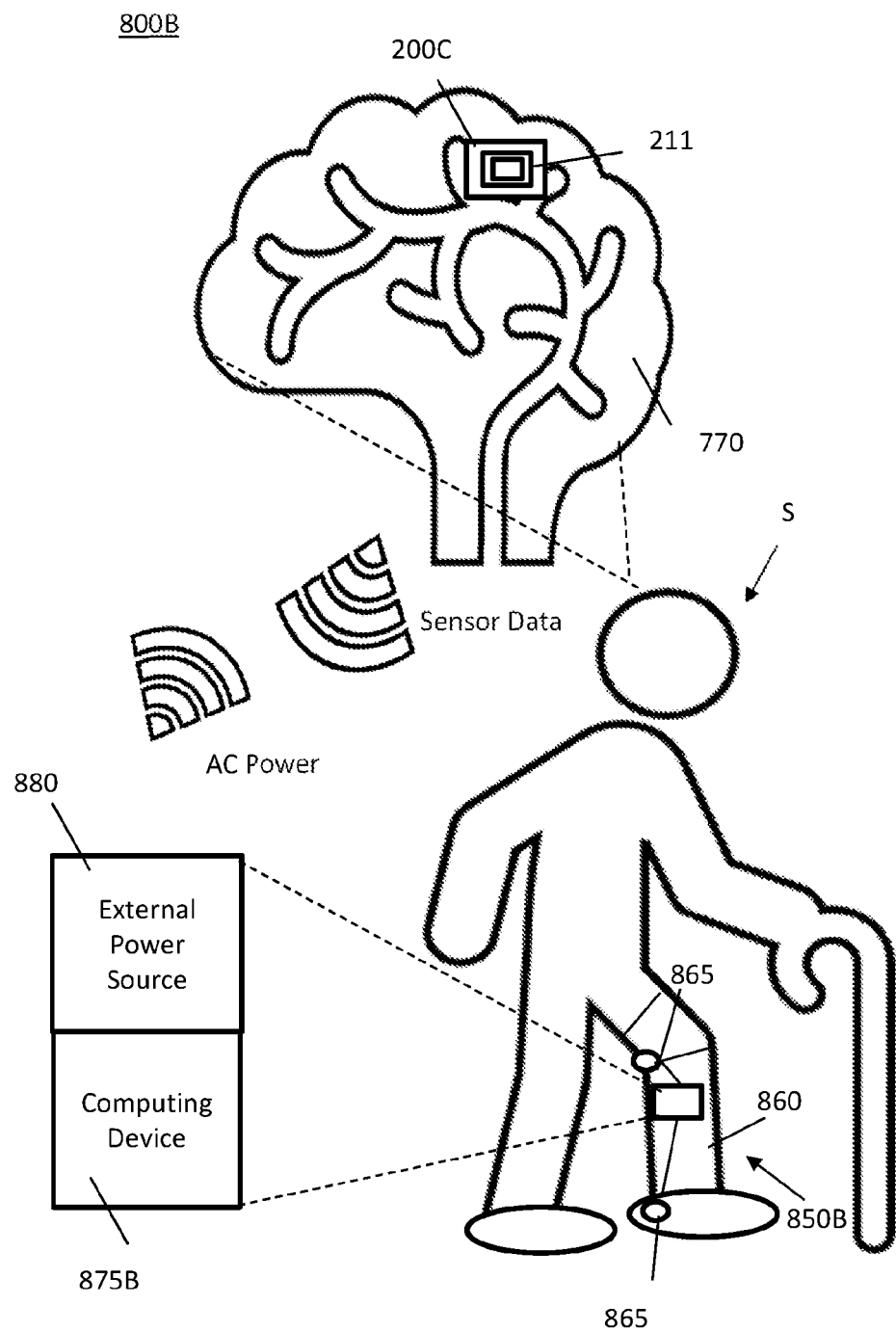
FIG. 8B illustrates a second MINI system for use with a prosthetic.

FIG. 8B illustrates a second MINI system 800B for use with a prosthetic device 860. The second MINI system 800B includes a remote system 850B which may comprise an external power source 880 and a computing device 875B attached or embedded in the prosthetic device 860. The computing device 875B may include a processor, memory, instructions recorded in the memory and/or one or more other components described in relation to computer system of FIG. 19. The prosthetic device 860 may include one or more actuators 865 which may be controlled based on the sensor neural data from the MINI device 200C wherein the remote system 850B and the MINI device 200C may be paired together for dedicated communications therebetween. In some embodiments, the MINI device 200C may still be capable of communicating with remote system 850A and 850B.

Figure 9A:
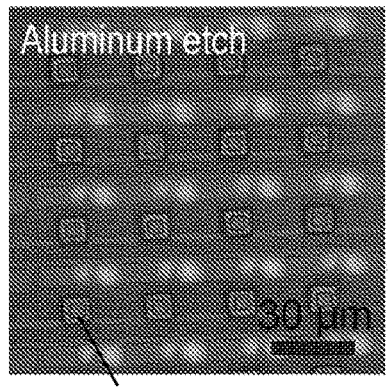
FIGS. 9A-9C illustrate steps for fabrication of an on-chip electrode array using gold electrodeposition.
Figure 9B:
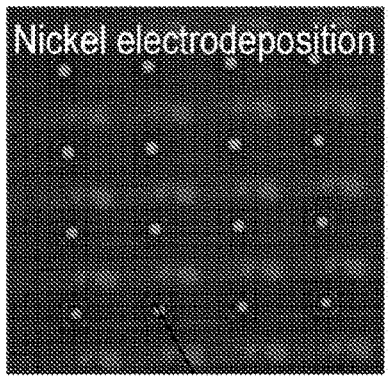
Figure 9C:
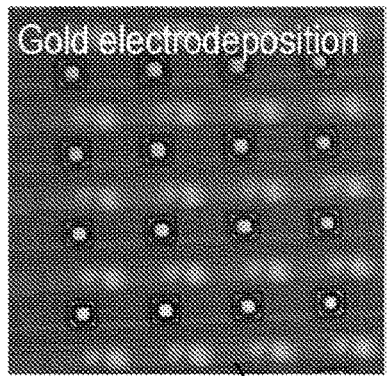

FIGS. 9A-9C illustrate steps for fabrication of an on-chip electrode array using gold electrodeposition. In FIG. 9A, step 900A may include using an electroplating protocol directly on the CMOS chip. Initially, a top metal layer 907 is removed by aluminum etching, as best shown in FIG. 9A. The top metal layer 907 may include aluminum and copper. By way of non-limiting example, a wet etch procedure for step 900A may be used.

In FIG. 9B, step 900B may include nickel (Ni) plating to form a nickel (Ni) layer 917. For example, the Ni layer may be applied using electrodeposition. In FIG. 9C, step 900C may include plating the Ni layer with gold (Au) to form a gold layer 927. For electroplating, an internal current source circuit, which is based on a current mirror circuit, was designed into the CMOS integrated circuit to draw constant current through the plating process. As shown in FIG. 9C, a self-aligned electrode array 210 was created.

Figure 9D:
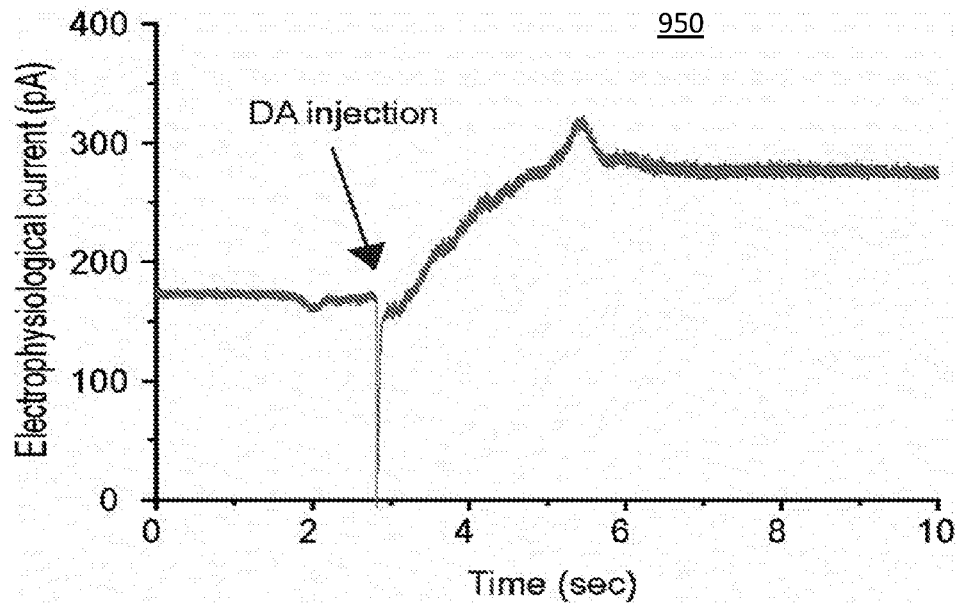
FIG. 9D illustrates a graphical representation of a dopamine measurement using on-chip electroplated electrodes.

FIG. 9D illustrates a graphical representation 950 of a dopamine measurement using on-chip electroplated electrodes according to the electrode created using the steps of FIGS. 9A-9C. A test for quality of the electroplated electrodes for on-chip recording and created in FIGS. 9A-8C was performed. To test the electrodes of FIGS. 9A-9C, a 500-μM of dopamine solution was applied to the CMOS chip's surface. This yielded a successfully recording as shown in FIG. 9D. The dopamine measurement does not directly reflect the action potential measurement for which these electrodes are intended but does test for stability and effectiveness of the fabrication process.

Figures 10A, 10B:
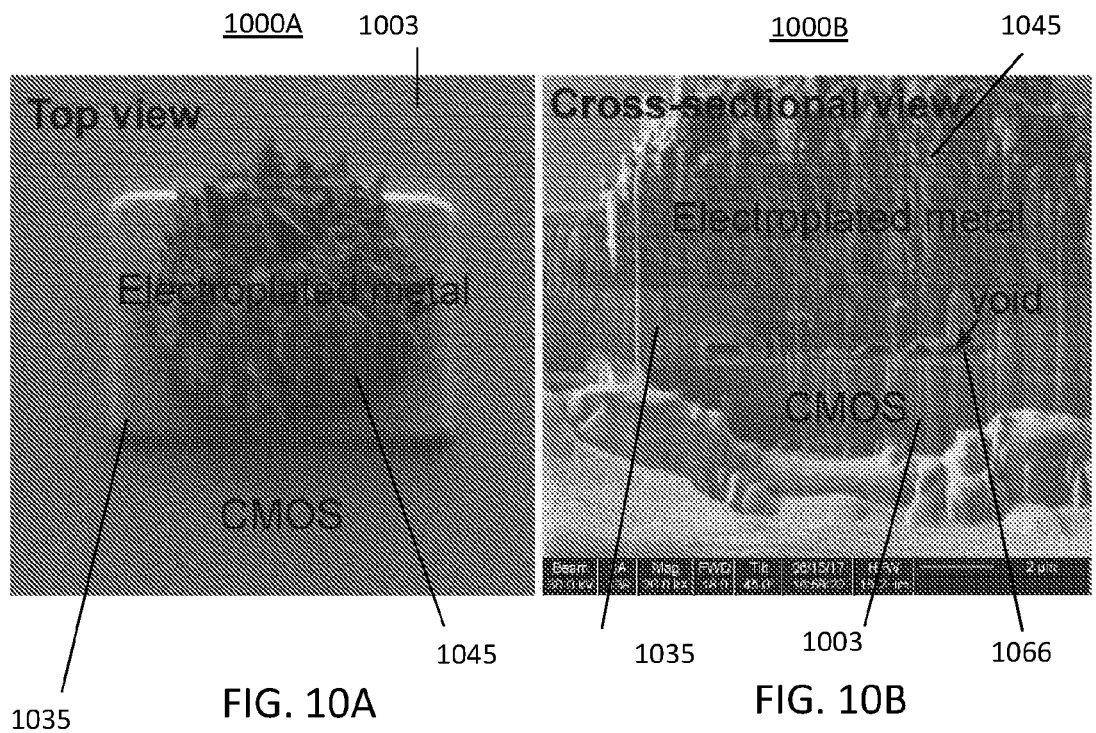
FIGS. 10A and 10B illustrate images of an electroplated electrode from a top view and cross-sectional view being cross-sectioned by a Focus Ion Beam (FIB)

FIGS. 10A-10B illustrate images 1000A and 1000B of an electroplated electrode 1045 from a top view and cross-sectional view by a Focus Ion Beam (FIB) which cuts the on-chip electrode. The FIB allows a scanning electron microscopy (SEM) image from an angle to be captured to show the cross-section of the on-chip electrode 1045. However, a negative aspect of the electroplating approach was observed. When testing the monolithic integration methods for manufacturing the MINI device described herein, reliability and robustness of the electrode were tracked. Despite the successful measurement shown in FIG. 9D, the test of the approach in FIGS. 9A-9C lacked stability and reliability. With respect to FIG. 10B the image 1000B of the electroplating process to create a pillar electrode 1045 in pillar 1035 was shown to cause instability. As shown in FIG. 10B, a small void 1066 (sub-microns) is clearly visible between the electroplated metal of electrode 1045 and the MINI device's CMOS chip or die 1003. This is undesirable because the electrolytic solution may leak into the void and cause damage to the MINI device's CMOS chip or die 1003.

Figures 11A, 11B, 11C:
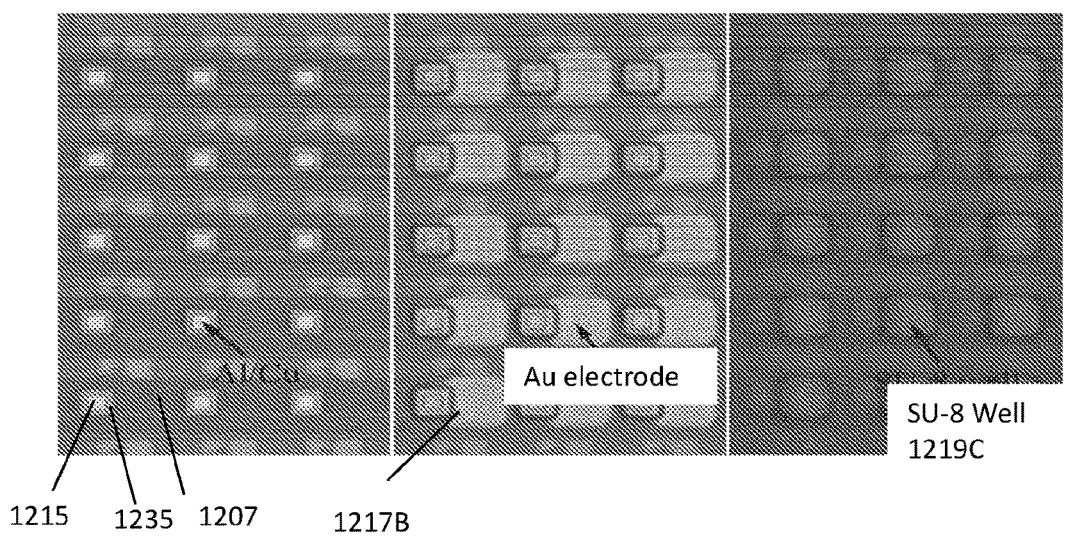
FIGS. 11A-11C illustrate top views of the post-CMOS processing steps for on-chip integration of planar electrodes and SU-8 wells.
Figures 12A, 12B, 12C:
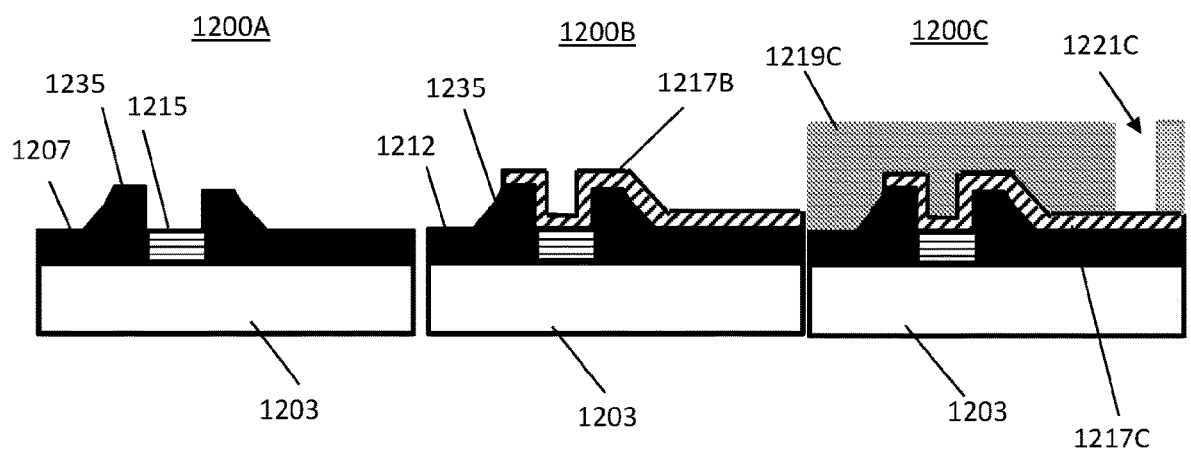
FIG. 12A-12C illustrate cross-sectional view of the steps for post-CMOS processing for on-chip integration of electrodes and SU-8 wells.

Post-CMOS procedures described herein may be used to fabricate on-chip electrodes 1045 of the electrode array 210 (FIG. 2D) using the standard photolithography process will be described in relation to FIGS. 12A-12C. Additionally, a post-CMOS procedure can be used to fabricate 1024 on-chip gold electrodes on the CMOS chip 1003, which can be used for action potential measurements as will be described in relation to FIGS. 13A-13B. FIGS. 12A-12C illustrate cross-sectional view of post-CMOS processing steps for on-chip integration of the planar electrodes and SU-8 wells 1219C. The top metal layer of CMOS chips is an aluminum-copper alloy in most conventional CMOS processes, which is inadequate for biosensing due to the aluminum's high reactivity to the electrolytic solutions. This causes not only high offsets in the electrophysiological recording that results in a high shot noise but may also result in damaging of the chip due to water leakage. Polarizable electrode materials, such as gold and platinum, are better suitable for the electrophysiological recording due to low reactivity. FIGS. 11A-11C illustrate top views of the steps for the post-CMOS processing for on-chip integration of planar electrodes and SU-8 wells as described in FIGS. 12A-12C. Therefore, FIGS. 11A-11C and FIGS. 12A-12C will be described together. Some reference numeral in FIGS. 11A-11C appear in the figures wherein like reference numerals reference the same elements in the figure as some elements cannot be seen in FIGS. 11A-11C.

FIGS. 11A and 12A illustrates step 1100A/1200A which includes creating a CMOS die 1203 having a first layer 1207 made of an oxide overlaid or formed on the material of the CMOS die 1203. A pillar 1235 is formed for each electrode. The center of the pad 1235 is open to a second (metal) layer 1215 which may include aluminum or aluminum and copper alloy, the second layer 1215 may be deposited on the CMOS die 1203 prior to the formation of the pad 1235 and the first (oxide) layer 1207. FIGS. 11B and 12B illustrates step 1100B/1200B which includes the CMOS die of FIG. 12A having a third layer 1217B overlaid on pillar 1235 and a portion of the first (oxide) layer 1207. The portion 1212 of layer 1207 (FIG. 12A) does not include an overlaid second layer 1217B. The second layer 1217B includes gold (Au).

FIGS. 11C and 12C illustrates step 1100C/1200C which includes the CMOS die 1203 of FIG. 12B having a third layer (gold layer) patterned using a lift-off process which is followed by the fabrication of a fourth layer 1219C which is overlaid on a portion of the third layer and the portion 1212 of the first layer 1207. The fourth layer 1219C may be a SU-8 layer. The channel in the pad is also filled with the fourth layer 1219C. A well 1221C is formed in a portion of the SU-8 layer which also overlay on the third layer 1217C. The well 1221C is an opening through the SU-8 layer 1219C down to the third layer 1217C made of gold, for example.

Figures 13A, 13B:
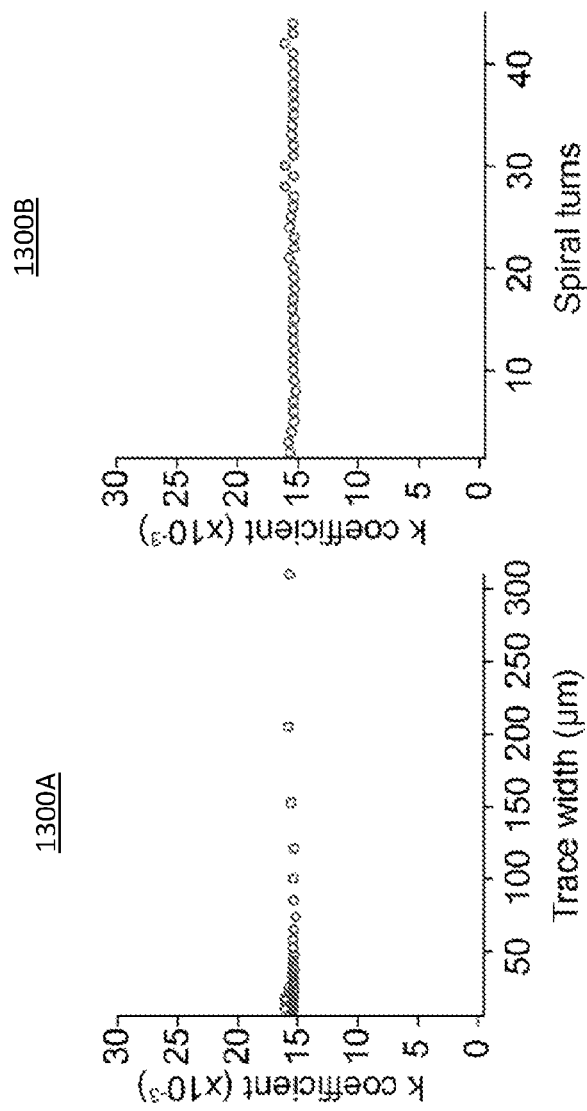
FIG. 13A illustrates a graphical representation of a constant coupling coefficient over various trace width.
FIG. 13B illustrates a graphical representation of a constant coupling coefficient over various spiral turns.
Figures 14A, 14B, 14C:
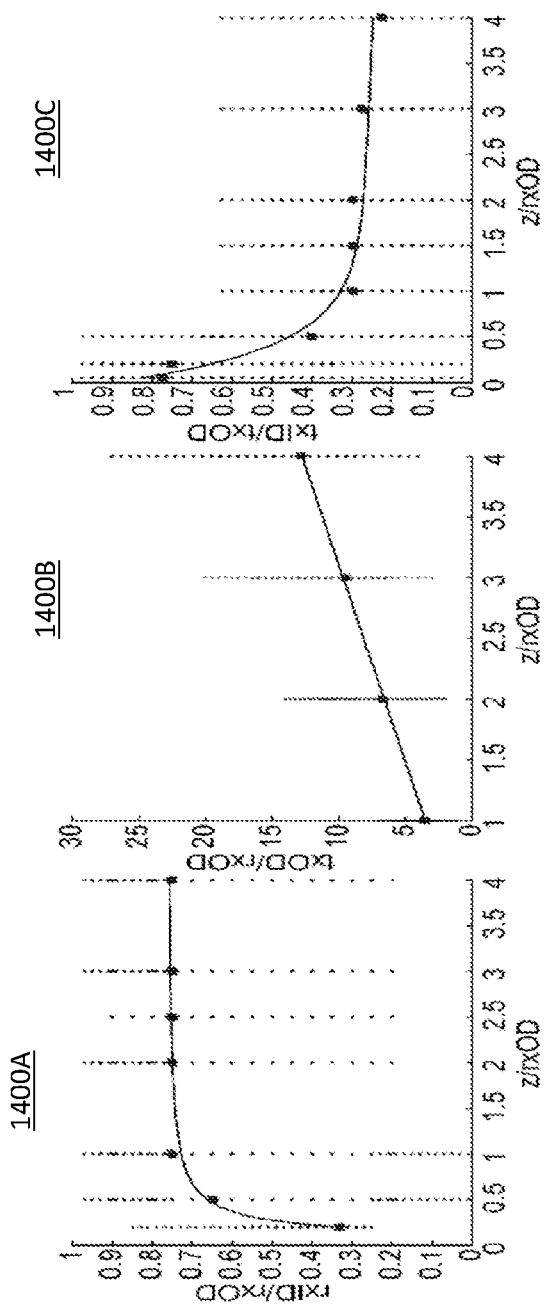
FIG. 14A illustrates optimal geometric values for square spiral coils as a function of spacing (z) to rxID/rxOD.
FIG. 14B illustrates optimal geometric values for square spiral coils as a function of spacing (z) to txOD/rxOD.
FIG. 14C illustrates optimal geometric values for square spiral coils as a function of spacing (z) to txID/txOD.

FIG. 13A illustrates a graphical representation 1300A of a constant coupling coefficient over various trace width. FIG. 13B illustrates a graphical representation 1300B of a constant coupling coefficient over various spiral turns. The RF planar coils may provide for the wireless power transfer. The RF planar coils may include square spiral coils. A study was conducted using ANSYS High-Frequency Structure Simulator (HFSS). Power transfer efficiency of an inductive link is dependent on the coupling coefficient, inductances, and series resistances. And the coupling coefficient (k) is known to be a function of distance, outer diameters, inner diameters, trace width (FIG. 13A), spacing, number of turns (FIG. 13B). Because of complex dependencies of parameters, determining the most optimal set of two coils is challenging task. In the analysis, the inventors' observed that among many parameters that affect the coupling coefficient for square spiral coils, the outer diameters (OD) and inner diameters (ID) of transmission (TX) and receiving (RX) coil are important factors to consider. So long as OD and ID are kept constant, the spacing, trace width, and the number of turns have little effect on the coupling coefficient (FIGS. 13A-13B). This observation is consistent with that of circular spiral coils. FIG. 14A illustrates a graphical representation 1400A of optimal geometric values for square spiral coils as a function of spacing (z) to rxID/rxOD. Using this observation, the optimal coupling coefficient based on a wide range of IDs and ODs is shown based on HFSS simulations. Using this data, a coil design methodology and Matlab macro for optimal square spiral coils was developed. The Matlab macro requires input parameters on the design constraints by the manufacturing capability and using these parameters, the macro scans all possible combination of receiving coil and transmission coil designs in seconds to output the set of design parameters which result in the highest power transfer efficiency. The coils may be fabricated using a standard photolithography to measure the power transfer efficiency.

FIG. 14B illustrates a graphical representation 1400B of optimal geometric values for square spiral coils as a function of spacing (z) to txOD/rxOD. FIG. 14C illustrates a graphical representation 1400C of optimal geometric values for square spiral coils as a function of spacing (z) to txID/txOD. The larger black dots represent the highest achievable k ($k_{max}$) at the certain z. Each black dot intersects a line. Each line has a first set of smaller dots indicating geometric values that result in higher than 0.9 $k_{max}$ and a second set of smaller dots which are below 0.9 $k_{max}$. The smaller dots below 0.9 kmax are at the upper and lower points of each line. In FIG. 14A, on the first line dots at and above 0.6 are the second set of smaller dots. The remaining dots on the first line are of the first set of dots. On the second line, the top 3 dots and the last 7 dots on the same line are part of the second set of dots. The remaining smaller dots are part of the first set of dots. Each graph at the max and min points include one or more dots of the second set of smaller dots.

Figure 15A:
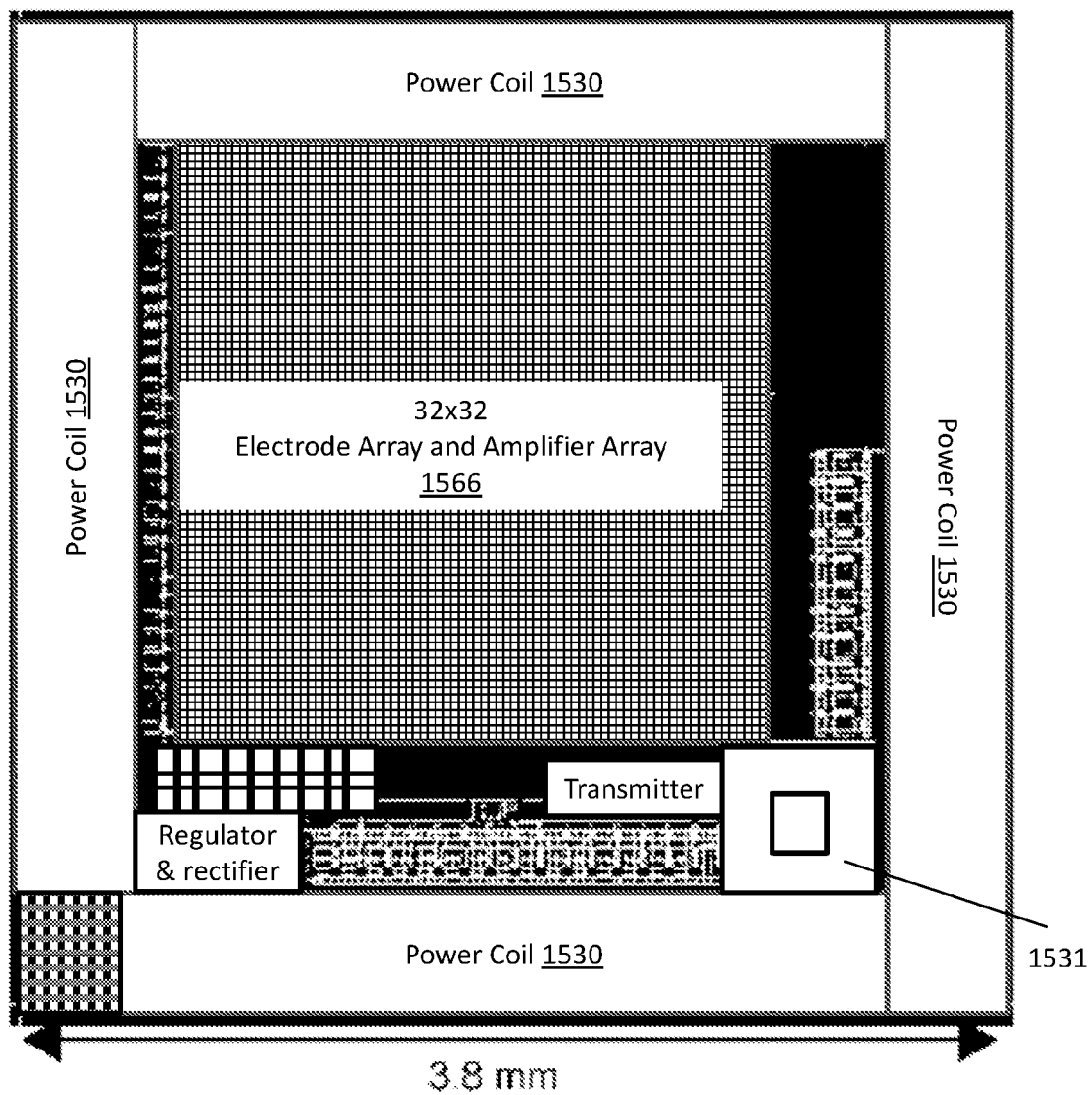
FIG. 15A illustrates a MINI device including a 1024-channel brain-machine interface chip designed in a standard 0.35-µm CMOS process.

FIG. 15A illustrates a MINI device 1500A including 1024-channel brain-machine interface chip designed in a standard 0.35-μm CMOS process. The amplifier and electrode pair array 1566 is shown as 32×32. However, the scalability allows more electrode/amplifier pairs to be added. The CMOS process and the MINI device 1500A may be fabricated using the 0.35-μm standard CMOS process. The MINI device 1500A may be configured as a 1000-ch monolithic brain-machine interface device. The chip may include 1024 on-chip amplifiers and 1024 on-chip electrodes pairs labeled 1566, on-chip wireless power coil 1530, on-chip wireless data coil 1531, transmitter, voltage regulator, and rectifier.

Figure 15B:
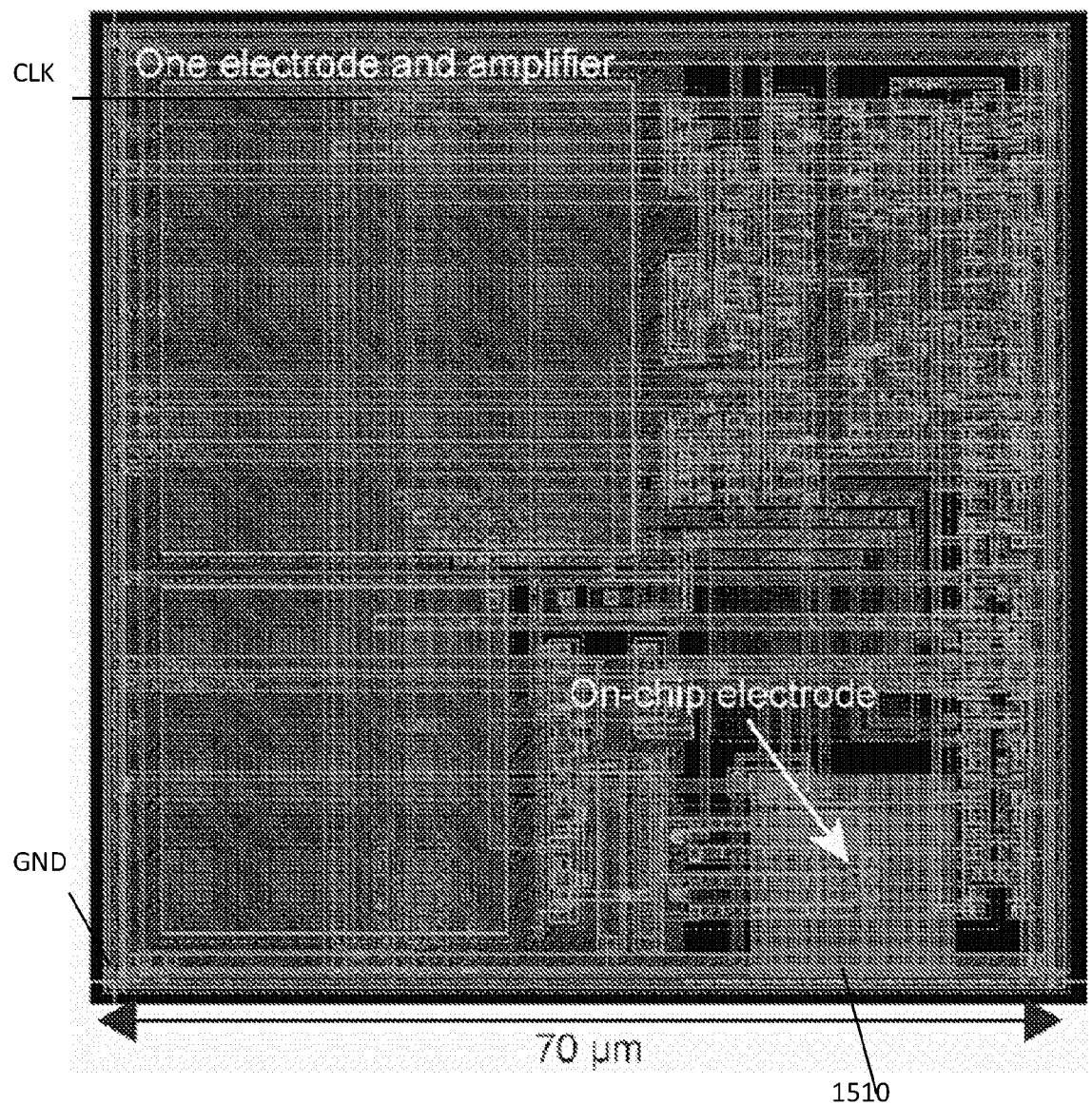
FIG. 15B illustrates an amplifier array for the MINI device of FIG. 15A.

FIG. 15B illustrates an amplifier and electrode pair array 1566 for the MINI device 1500A of FIG. 15A. Each amplifier and electrode pair 1566 may occupy approximately 70 μm×70 μm area, as seen in FIG. 15B, and the entire chip occupies approximately 3.8 mm×3.8 mm. The ground GND and clock CLK are shown.

Figures 16A, 16B:
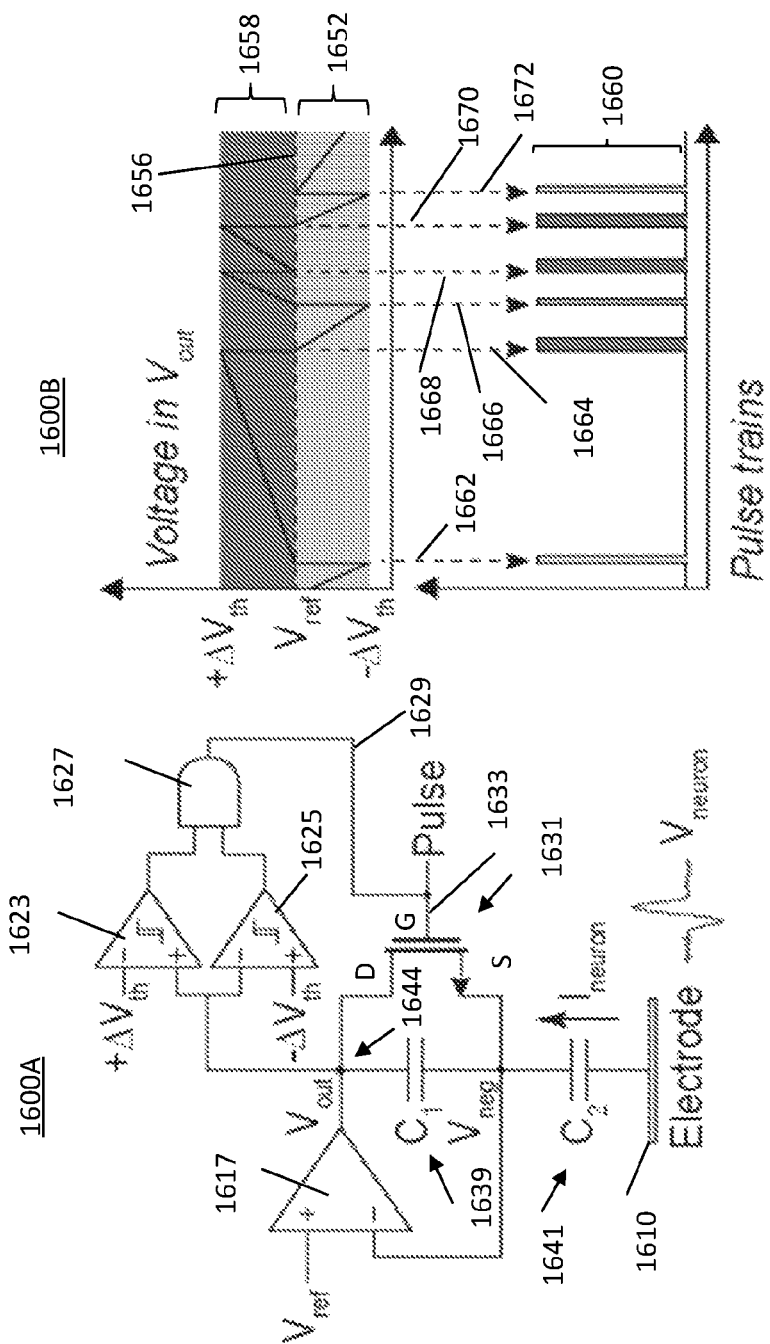
FIG. 16A illustrates a schematic diagram of a delta-modulator for compressive neural recordings, where the schematic includes two comparators which trigger reset pulse when a change in voltage above/below preset thresholds is detected.
FIG. 16B illustrates a graphical representation of voltage rise in $V_{out}$ above $V_{ref}+\Delta V_{th}$ causing a thick digital pulse and a voltage drop below $V_{ref}-\Delta V_{th}$ causes a thin digital pulse.

FIG. 16A illustrates a schematic diagram of a delta-modulator 1600A for compressive neural recordings, where the schematic includes two comparators 1623 and 1625 which trigger a reset pulse on line 1633 when a change in voltage above/below preset thresholds is detected. A typical neural recording system consists of a voltage amplifier and an analog-to-digital converter (ADC). The neural potential is amplified using the voltage amplifier and the ADC converts the analog values to digital values for data processing and transmission. However, this method introduces a large power consumption from the ADC and a large area consumption due to the size of ADC, which are both undesirable for low-power implant devices. Unlike a typical neural recording system, the MINI device may include a delta-modulator, in some embodiments, which does not require an ADC and has a high data compression capability.

The neural signal detected at the electrode 1610, $V_{neuron}$, will generate an input current, $I_{neuron}$, through input capacitor ($C_2$) 1641. This current will be integrated across the feedback capacitor ($C_1$) 1639 and change the output voltage $V_{out}$. The output voltage $V_{out}$ can be expressed as the following: $\Delta V_{out} = c_2/c_1 \times \Delta V_{neuron}$. The $V_{out}$ node 1644 will be connected to two comparators 1623 and 1625 which detect an increase above $\Delta V_{th}$ or decrease below $\Delta V_{th}$ in $V_{out}$ during a detection cycle. Comparator 1623 receives +$\Delta V_{th}$ and comparator 1625 receives −$\Delta V_{th}$. The output of each of comparators 1623 and 1625 are input to an AND gate 1627. The output 1629 is sent to the gate G of transistor 1631 which may be a metal oxide semiconductor field effect transistor (MOSFET), on line 1633. The source S of the transistor 1631 is coupled to a node between capacitors 1641 and 1639, where the voltage $V_{neg}$ results. The $V_{neg}$ node feeds the comparator 1617 which receives $V_{ref}$ at one terminal and $V_{neg}$ at a second terminal. The comparator 1617 produces a voltage $V_{out}$ at node 1644.

FIG. 16B illustrates a graphical representation 1600B of a voltage rise in voltage $V_{out}$ above $V_{ref}$ (in range 1652) plus $\Delta V_{th}$ (in range 1658) causing a thick digital pulse (i.e., pulses 1654, 1668, and 1670) and a voltage drop below $V_{ref} - \Delta V_{th}$ causes a thin digital pulse (i.e., pulses 1662, 1666, and 1672). The ranges 1652 and 1658 are separated by dashed line 1656. In FIG. 16B an example of 6 cycles is illustrated, represented by pulse train 1660. The voltage increase in $V_{out}$ above $V_{ref} + \Delta V_{th}$ due to a −$V_{neuron}$ results in a wide pulse (two 1-bits). Likewise, the voltage decrease below $V_{ref} - \Delta V_{th}$ due to a +$\Delta V_{neuron}$ results in a short pulse (single 1-bit). The width of pulses can be later used to identify the polarity of recorded $\Delta V_{neuron}$. Whenever either one of the threshold conditions ($V_{ref} \pm \Delta V_{th}$) is met, the pulse will become high to reset the capacitor ($C_1$) 1639 by an AND 1627 logic, establishing $V_{out} = V_{neg} = V_{ref}$ to re-initiate a new detection cycle.

FIG. 17A illustrates a neural signal sampling 1700A based on a delta-modulator and traditional neural recording system wherein the spike is an example of 1-mV neural spike, triangles (▲) indicate where the delta-modulator will sample, and crosses (x) show where the traditional system will sample. A simulation study of the delta-modulator is shown in FIGS. 17A-17C. In this study, an example action potential with a 1-mV peak, is inputted to the delta-modulator and to a traditional neural recording system. Typically, electrocorticography (ECoG) measurements yield 30 μV-5 mV of neural spikes. A conventional neural recording system samples the neural signal at a constant-rate, as shown by the crosses (x) in FIG. 17A. The delta-modulator is only sensitive to the change in voltage and thus will not measure small micro-volts of fluctuation due to noise. The delta-modulator's sampling is indicated as triangles (▲) in FIG. 17A. Each delta-modulator's sample immediately generates single or two 1-bits pulses in pulse trains as shown in FIG. 17B.

FIG. 17B illustrates the pulse train 1700B based on sampling the neural signal based on the delta-modulator's samples. In this example, the delta-modulator generates 57 bits of data or pulse trains which can be used to reconstruct the original signal with close matching. FIG. 17C illustrates the reconstruction of the neural signal 1700C based on the delta-modulator's samples. FIG. 17D illustrates the reconstruction of a neural signal 1700D based on the constant-rate sampling. As can be seen, the signal 1700C and 1700D closely match each other. However, the regular constant-rate sampling generates 49 samples which correspond to 588 bits of data assuming using a 12-bit ADC. This is over 10 times of data compression. The comparison of signal reconstructions from each method reveals a comparable or better resemblance to the original grey signal at the spike from the delta-modulator. Therefore, using the delta-modulator, compressive sensing of neural signals without distortion may be achieved.

Figure 18:
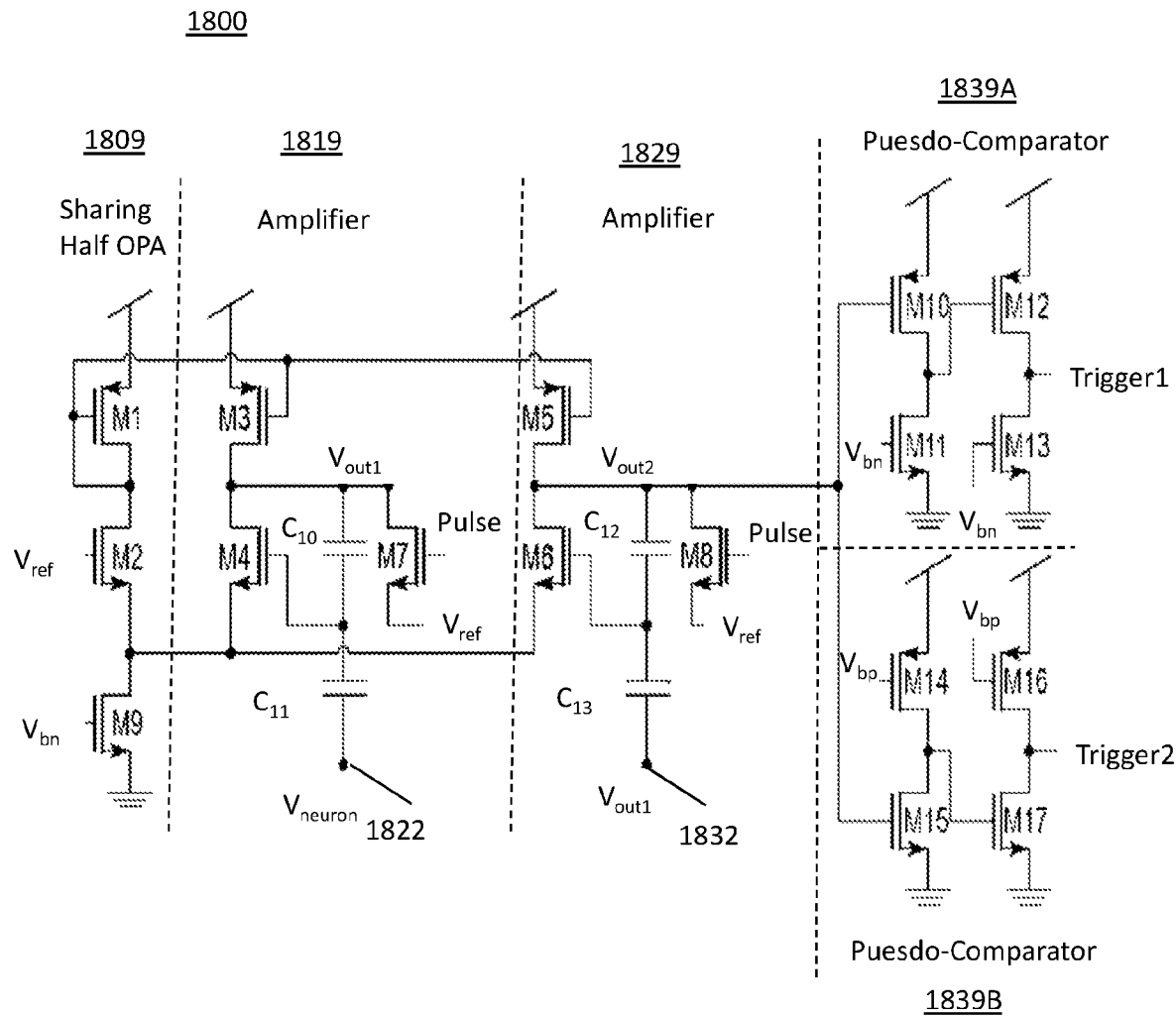
FIG. 18 illustrates a core circuit schematic diagram for a delta-modulator which uses a simple operational amplifier (OPA) design and two pseudo-comparators.

FIG. 18 illustrates a core circuit schematic diagram for a delta-modulator 1800 which uses a simple operational amplifier (OPA) 1809 and two pseudo-comparators 1839A and 1839B. The circuit design of the delta-modulator 1800 may satisfy two conditions. The first condition may be associated with the size of the delta-modulator 1800 to fit in a small area. The second condition may include minimal power consumption to operate the MINI device wirelessly without an integrated battery. Thus, the MINI devices may use a simple operational amplifier (OPA) 1809 and two pseudo-comparators 1839A and 1839B.

Complicated operational amplifier (OPA) designs can have a high gain and bandwidth which requires high power consumption and a large footprint. To minimize mismatch between the inverting and noninverting halves of the OPA 1809, it may be desirable to invest relatively large areas to input and load transistors. Because ~200 V/V of gain and −50 kHz bandwidth is easily achievable with a simple OPA design, the MINI device may use 5-transistor-based OPAs to dedicate large areas to transistors, denoted as M1-M4. In some embodiments, 2-stage amplifiers, such as amplifiers 1819 and 1829 may be used to set the overall gain between 5,000-16,000 V/V. In order to efficiently use the silicon area, a half-sharing OPA 1809 may be used. Node 1822 receives the neuron or neural signal denoted as $V_{neuron}$. The transistors M1-M17 may be MOSFET type transistors.

Amplifier 1819 and amplifier 1829 share the non-inverting half of the amplifier (OPA) 1809 wherein the amplifier (OPA) 1809 may include a plurality of transistors, denoted as M1, M2, and M9. Amplifier 1819 is a first stage amplifier and may include transistors M3, M4 and M7 with capacitors C10 and C11. Capacitor C10 is tied to the node $V_{out1}$ and the gate of transistor M4. The drains of transistors M3 and M4 are tied together to node $V_{out1}$. The drain of transistor M7 is tied to node $V_{out1}$. The source of transistors M7 and M8 received voltage $V_{ref}$. The gate of transistors M7 and M8 receive a pulse signal. The gate of transistors M2 and M9 receive voltages $V_{ref}$ and $V_{bn}$, respectively. The bias voltage $V_{bn}$ may be around 0.5 V and set internally within the chip. The source of transistor M2 and the drain of transistor M9 are tied together and to the source of transistor M4 and M6.

The amplifier 1829 is a second-stage amplifier with transistors M5, M6 and M8 and capacitors $C_{12}$ and $C_{13}$. The transistors M5 and M3 have their gates tied to the gate of transistor M1. The amplifier 1819 and 1929 generally mirror each other. However, node 1822 is tied to the gate of transistor M4 through capacitor $C_{11}$. The node for voltage $V_{out1}$ at the drains of transistors M3, M4 and M7 may also be tied to node 1832.

The node for $V_{out2}$ is tied to the drains of transistors M5, M6 and M8. Capacitor $C_{12}$ is tied to the $V_{out2}$ node and the gate of transistor M6. The voltage $V_{out2}$ is tied to the gates of transistors M10 and M15 of pseudo-comparators 1839A and 18398, respectively.

Comparators are typically made using a fully-differential amplifier, but this can consume large power and area. Instead, a first and second pseudo-comparators 1839A and 18398, including transistors M10-M17, may be used which includes two cascading common-source amplifiers operating in weak to moderate inversion for low-power. The benefit of the first pseudo-comparator 1839A may be that the process variation in the transistor size has minimal influence on the performance, in contrast to a fully-differential amplifier which has little tolerance to the transistor size variation.

The drains of transistors M14 and M15 are tied to the gate of transistor M17. The gate of transistors M14 and M16 receive voltage $+V_{bp}$. The drains of transistors M16 and M17 may produce trigger2 such as through a NAND component (not shown). The bias voltage $V_{bp}$ is also set internally within the chip.

The drains of transistors M10 and M11 are tied to the gate of transistor M12. The gate of transistors M11 and M13 receive voltage $-V_{bn}$. The drains of transistors M12 and M13 may produce trigger1 such as through a NAND component.

The first pseudo-comparator 1839A, including transistors M10-M13, is for the high threshold ($V_{ref}+\Delta V_{th}$) and the second pseudo-comparator 18398, including transistors M14-M17, is for the low threshold ($V_{ref}-\Delta V_{th}$). A pulse will be generated by merging both the signals represented as trigger1 and trigger2 using a NAND gate (not shown), for example. When either threshold conditions are met, the pulse needs to stay high for a fixed duration to avoid premature resetting. To achieve this, a latch and D flip-flop may be used. The voltage $V_{th}$ is a threshold voltage.

The estimated power consumption of the delta-modulator is ~700 nW (nano Watts) under 3.3-V power with the 200-nA biasing on the amplifier (OPA) 1809 and 50-nA biasing for each common-source amplifier. The power consumption from digital circuits is expected to be negligible compared to the analog circuits.

The neural sensing circuits and wireless power transmission will have an impact on not only the neural interface but also other sensor applications. Embodiments herein may use low-power sensing circuits using half-shared structure. This circuit topology is also applicable for high-throughput applications, effectively reducing the power consumption in half. This efficient low-power amplifier design uses a half-shared structure for preserving power.

The long-term recordings from large neuron populations in the sensory cortex and primary motor cortex reveal the detailed information encoded into neural signals and guide research in restoring the cognitive and motor behaviors by stimulating the cortex with high-throughput BMI devices. In such devices, the quality of information relies on the density and resolution of neural signals being measured/stimulated. Thus, MINI device provides a brain-machine interface configured for large-scale recording capabilities and high-throughput.

Figure 19:
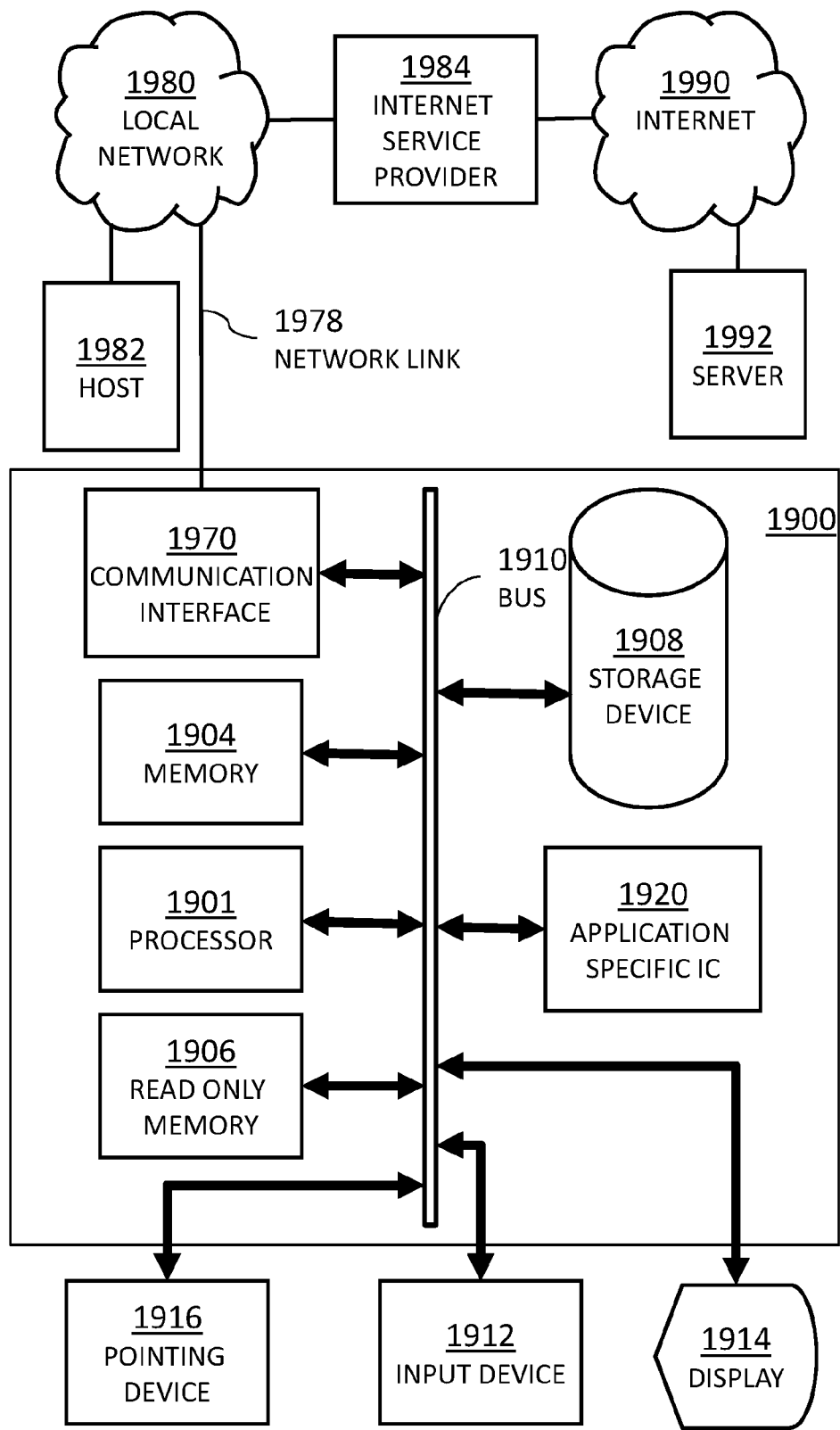
FIG. 19 illustrates a block diagram of computational hardware.

FIG. 19 is a block diagram that illustrates hardware of a computer system 1900 upon which a system of the embodiments may employ. Computer system 1900 includes a communication mechanism such as a bus 1910 for passing information between other internal and external components of the computer system 1900. A computer device as used herein may include less than the components of the computer system 1900. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1900, or a portion thereof, constitutes a means for performing one or more steps of one or more methods described herein. For example, the fabrication steps described herein may be computer implemented such that a machine for causing formation of a substrate (silicon-based substrate), TSVs, electrodes, coils, the IC layer(s), electrodeposition, plating, etching, etc. to be performed to create the MINI device as described herein. Other computer implemented methods may include sensing neural signals by the MINI device and communicating the signals to an analysis device, such as for testing, calibration, troubleshooting, etc. Other computer implemented methods may include sensing neural signals of a subject and communicating the neural signals to a prosthetic device including a computing module and control actuators. The prosthetic device may analyze the neural signals and control one or more control actuators of the prosthetic device to automatically control the operation and/or movement of the prosthetic device.

A sequence of binary digits constitutes digital data that is used to represent a number or code for a character. A bus 1910 includes many parallel conductors of information so that information is transferred quickly among devices coupled to the bus 1910. One or more processors 1901 for processing information are coupled with the bus 1910. A processor 1901 performs a set of operations on information. The set of operations include bringing information in from the bus 1910 and placing information on the bus 1910. The set of operations also typically include comparing two or more units of information, shifting positions of units of information, and combining two or more units of information, such as by addition or multiplication. A sequence of operations to be executed by the processor 1901 constitutes computer instructions.

Computer system 1900 may also include a memory 1904 coupled to bus 1910. The memory 1904, such as a random access memory (RAM) or other dynamic storage device, stores information including computer instructions. Dynamic memory allows information stored therein to be changed by the computer system 1900. RAM allows a unit of information stored at a location called a memory address to be stored and retrieved independently of information at neighboring addresses. The memory 1904 is also used by the processor 1901 to store temporary values during execution of computer instructions. The computer system 1900 may also include a read only memory (ROM) 1906, non-volatile persistent storage device or static storage device coupled to the bus 1910 for storing static information, including instructions, that is not changed by the computer system 1900. The ROM 1906 may be a secure byte-addressable memory (storage) device or a direct-access for files (DAX) memory device. Also coupled to bus 1910 may be a non-volatile (persistent) storage device 1908, such as a magnetic disk or optical disk, for storing information, including instructions, that persists even when the computer system 1900 is turned off or otherwise loses power.

Information, including instructions, is provided to the bus 1910 for use by the processor from an external input device 1912, such as a keyboard containing alphanumeric keys operated by a human user, or a sensor. A sensor detects conditions in its vicinity and transforms those detections into signals compatible with the signals used to represent information in computer system 1900. Other external devices coupled to bus 1910, may be used primarily for interacting with humans, may include a display device 1914, such as a cathode ray tube (CRT) or a liquid crystal display (LCD), for presenting images, and a pointing device 1916, such as a mouse or a trackball or cursor direction keys, for controlling a position of a small cursor image presented on the display 1914 and issuing commands associated with graphical elements presented on the display 1914.

In the illustrated embodiment, special purpose hardware, such as an application specific integrated circuit (IC) 1920, is coupled to bus 1910. The special purpose hardware is configured to perform operations not performed by processor 1901 quickly enough for special purposes. Examples of application specific ICs include graphics accelerator cards for generating images for display 1914, cryptographic boards for encrypting and decrypting messages sent over a network, and interfaces to special external devices, such as robotic arms and medical scanning equipment that repeatedly perform some complex sequence of operations that are more efficiently implemented in hardware.

Computer system 1900 may also include one or more instances of a communications interface 1970 coupled to bus 1910. Communication interface 1970 may provide a two-way communication coupling to a variety of external devices that operate with their own processors, such as printers, scanners and external disks. In general, the coupling may be with a network link 1978 that is connected to a local network 1980 to which a variety of external devices with their own processors are connected. For example, communication interface 1970 may be a parallel port or a serial port or a universal serial bus (USB) port on a personal computer. In some embodiments, communications interface 1970 may be an integrated services digital network (ISDN) card or a digital subscriber line (DSL) card or a telephone modem that provides an information communication connection to a corresponding type of telephone line. In some embodiments, a communication interface 1970 may be a cable modem that converts signals on bus 1910 into signals for a communication connection over a coaxial cable or into optical signals for a communication connection over a fiber optic cable. As another example, communications interface 1970 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1970 sends and receives electrical, acoustic or electromagnetic signals, including infrared and optical signals, that carry information streams, such as digital data. In some embodiments, the communications interface 1970 may be compatible with telemetry link communications for receiving communications from the MINI device.

The term computer-readable medium is used herein to refer to any medium that participates in providing information to processor 1901, including instructions for execution. Such a medium may take many forms, including, but not limited to, non-volatile media, volatile media and transmission media. Non-volatile media include, for example, optical or magnetic disks, such as storage device 1908. Volatile media include, for example, dynamic memory 1904. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1901, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1901, except for carrier waves and other signals.

Logic encoded in one or more tangible media includes one or both of processor instructions on a computer-readable storage media and special purpose hardware, such as ASIC 1920.

Network link 1978 typically provides information communication through one or more networks to other devices that use or process the information. For example, network link 1978 may provide a connection through local network 1980 to a host computer 1982 or to equipment 1984 operated by an Internet Service Provider (ISP). ISP equipment 1984 in turn provides data communication services through the public, world-wide packet-switching communication network of networks now commonly referred to as the Internet 1990. A computer called a server 1992 connected to the Internet provides a service in response to information received over the Internet. For example, server 1992 provides information representing video data for presentation at display 1914.

The invention is related to the use of computer system 1900 for implementing some of the techniques described herein. The system 1900 may be used for analyzing the recorded or sensed neural signals by the MINI device 200A. According to one embodiment of the invention, those techniques are performed by computer system 1900 in response to processor 1901 executing one or more sequences of one or more instructions contained in memory 1904. Such instructions, also called software and program code, may be read into memory 1904 from another computer-readable medium such as storage device 1908. Execution of the sequences of instructions contained in memory 1904 causes processor 1901 to cause one or more of the method steps described herein. For examples, the methods for fabrication may be computer-implemented to cause designated machines or CMOS fabrication devices to perform the patterning, electroplating, etching, layering of materials, etc. In alternative embodiments, hardware, such as application specific integrated circuit 1920, may be used in place of or in combination with software to implement the invention. Thus, embodiments of the invention are not limited to any specific combination of hardware and software.

The signals transmitted over network link 1978 and other networks through communications interface 1970, carry information to and from computer system 1900. Computer system 1900 may send and receive information, including program code, through the networks 1980, 1990 among others, through network link 1978 and communications interface 1970. In an example using the Internet 1990, a server 1992 transmits program code for a particular application, requested by a message sent from computer 1900, through Internet 1990, ISP equipment 1984, local network 1980 and communications interface 1970. The received code may be executed by processor 1901 as it is received or may be stored in storage device 1908 or other non-volatile storage for later execution, or both. In this manner, computer system 1900 may obtain application program code in the form of a signal on a carrier wave.

Various forms of computer readable media may be involved in carrying one or more sequence of instructions or data or both to processor 1901 for execution. For example, instructions and data may initially be carried on a magnetic disk of a remote computer such as host 1982. The remote computer loads the instructions and data into its dynamic memory and sends the instructions and data over a telephone line using a modem. A modem local to the computer system 1900 receives the instructions and data on a telephone line and uses an infra-red transmitter to convert the instructions and data to a signal on an infra-red a carrier wave serving as the network link 1978. An infrared detector serving as communications interface 1970 receives the instructions and data carried in the infrared signal and places information representing the instructions and data onto bus 1910. Bus 1910 carries the information to memory 1904 from which processor 1901 retrieves and executes the instructions using some of the data sent with the instructions. The instructions and data received in memory 1904 may optionally be stored on storage device 1908, either before or after execution by the processor 1901.

Figure 20:
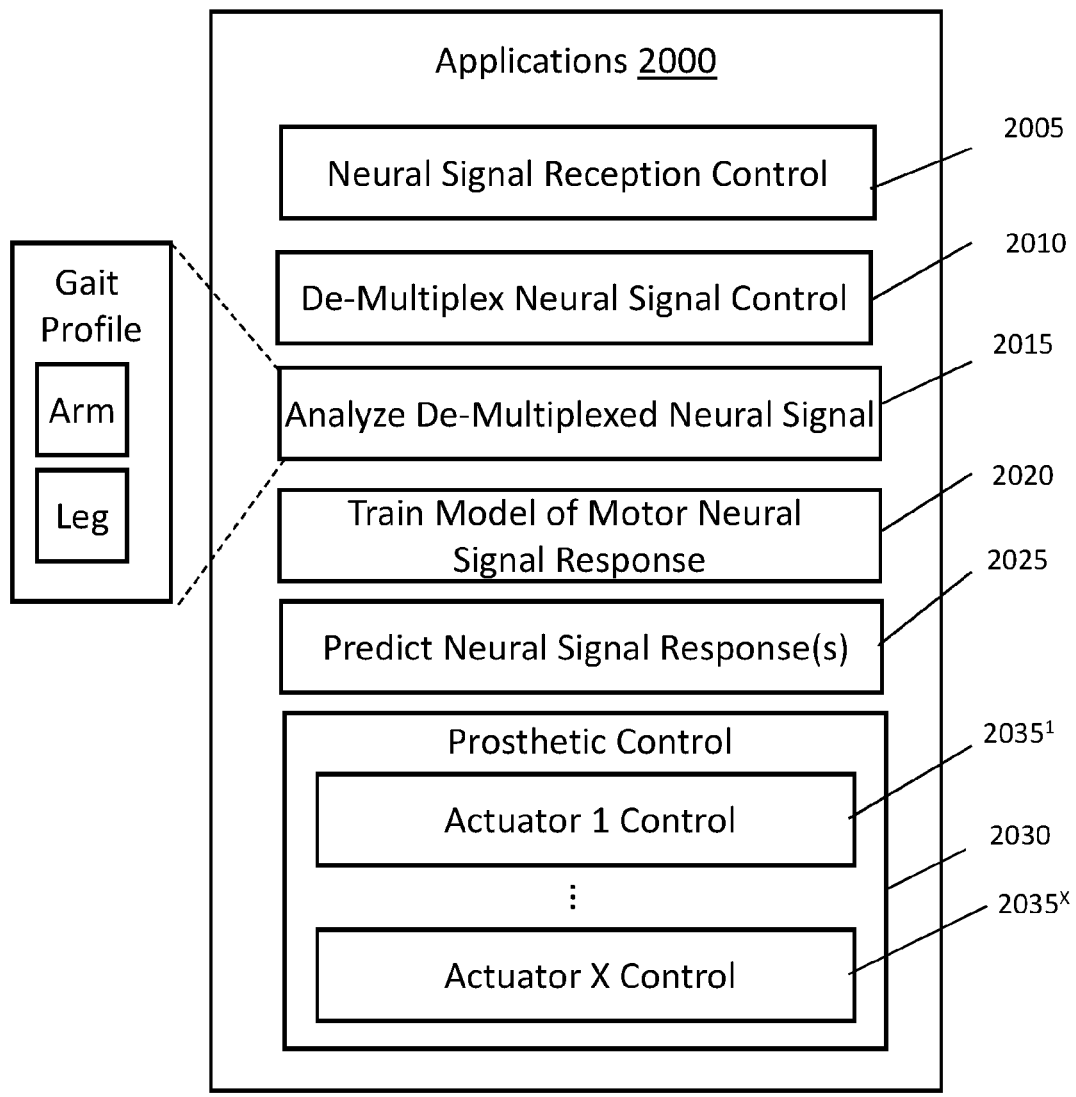
FIG. 20 illustrates program instructions for use with a prosthetic device.

FIG. 20 illustrates program instructions (applications) 2000 for use with a prosthetic device 860. The applications 2000 may provide instructions for neural signal reception control 2005 at the prosthetic device 860 or remote computer system 875A. The neural signal reception control 2005 instructions may include reception control by a receiver and demodulation or decompression of the modulated data signal. The applications may include instructions for de-multiplex neural signal control 2010 to de-multiplex the multiplexed data signal based on the multiplex protocol, such as TDMA. The applications 2000 may include instructions to analyze the de-multiplexed neural signal 2015. Depending on the number of electrodes, the signal derived from each electrode of the array is individually multiplexed so that during analysis of those neural signals associated with the sensory cortex and/or the primary motor cortex to restore motor functions such as through the use of a prosthetic device (FIG. 8B). In some embodiments, the neural signal control instructions may assist in enhancing or providing cognitive control.

The instructions may include instructions to train a model of motor neural signal responses 2020. The model may first be derived based on a population of subjects with similar motor deficiencies and/or then trained during operation from neural signals derived by the subject. Training may be accomplished by neural networks, Bayesian networks, or other computer learning systems. The instructions may include instructions to predict neural signal response(s) 2025. The collection of neural signals received from the electrode array 210 may be used to predict a neural signal response for the current set of neural signals. As can be appreciated, the neural signals are continually updated requiring further prediction. The instructions may include instructions to control the prosthetic 2030. The instructions may include actuator 1 control instructions $2035^1$ to actuator X control instructions $2035^X$ where X is an integer number greater than 1 and corresponds to the number of actuators integrated in the prosthetic device.

As described in relation to FIG. 8B. the prosthetic device may be capable of automated articulation through actuator controllers, such as at hinged joints. The instructions to control the prosthetic 2030 may control one or more actuators at any one time. In the example, a leg prosthetic device is shown. The instructions at any point in time may control one or all actuators based on the collection of neural signals.

The instructions to analyze the de-multiplexed neural signal 2015 may include a gait profile such as for an arm and/or leg depending on the prosthetic device. The arm may include one or more of fingers with finger joint actuators, a wrist with wrist actuators, an elbow with elbow actuators, and a shoulder with shoulder actuators. The leg may include one or more of a foot with toe actuators, an ankle with ankle actuators, a knee with knee actuators, and a hip with hip actuators.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another.

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

Therefore, the breadth and scope of the subject matter provided herein should not be limited by any of the above explicitly described embodiments. Rather, the scope of the embodiments should be defined in accordance with the following claims and their equivalents.

REFERENCES

R. R. Harrison, "Designing Efficient Inductive Power Links for Implantable Devices," in 2007 *IEEE International Symposium on Circuits and Systems*, 2007, pp. 2080-2083.

Wei Tang and E. Culurciello, "A pulse-based amplifier and data converter for bio-potentials," in 2009 *IEEE International Symposium on Circuits and Systems*, 2009, pp. 337-340.

C. L. Rogers, J. G. Harris, J. C. Principe, and J. C. Sanchez, "A Pulse-Based Feature Extractor for Spike Sorting Neural Signals," in 2007 *3rd International IEEE/EMBS Conference on Neural Engineering*, 2007, pp. 490-493.

K. A. White, G. Mulberry, and B. N. Kim, "Multifunctional High-Throughput Single-Cell Analysis using Reconfigurable Amplifier Array," *Biophys. J.*, vol. 112, no. 3, p. 461a, February 2017.

B. N. Kim, A. D. Herbst, S. J. Kim, B. A. Minch, and M. Lindau, "Parallel recording of neurotransmitters release from chromaffin cells using a 10×10 CMOS IC potentiostat array with on-chip working electrodes," *Biosens. Bioelectron.*, vol. 41, pp. 736-744, 2013.

What is claimed is:

1. A device comprising:
a chip, the chip comprising:
an integrated circuit (IC) being embedded in a frontplane layer and comprising a plurality of amplifiers configured to amplify received neural signals from a monitored subject, and a radio data signal generator configured to process the amplified neural signals and generate a multiplexed digital signal, the frontplane layer comprising an external surface;
radio-frequency (RF) planar coils embedded in a backplane layer, and electrically connected to the IC, the RF planar coils being configured for wireless transmission of the multiplexed digital signal to a remote wireless device and being configured to receive wireless power signals to power the IC; and
a plurality of on-chip electrodes integrated on a top layer of the integrated circuit and configured to directly sense the neural signals of the subject and provide the neural signals to the plurality of amplifiers, wherein the plurality of on-chip electrodes comprise a pillar electrode array or a planar electrode array with the plurality of on-chip electrodes comprising at least 1000 electrodes,
wherein the chip comprising the frontplane layer, the backplane layer and the plurality of on-chip electrodes form a wireless, battery-less monolithically-integrated neural interface (MINI) device configured to be implanted.

2. The device of claim 1, further comprising conductive vias for electrically connecting the IC to the RF planar coils.

3. The device of claim 2, wherein each conductive vias comprising a through-silicon via.

4. The device of claim 2, wherein the integrated circuit comprises a top layer and a bottom layer, wherein the conductive vias are generally coupled to the top layer on opposite sides of the bottom layer.

5. The device of claim 1, wherein each on-chip electrode of the plurality of on-chip electrodes comprising a tungsten core and a gold plating surrounding the tungsten core.

6. The device of claim 1, wherein the plurality of on-chip electrodes comprises one of 1000 electrodes and 1024 electrodes.

7. The device of claim 1, wherein
the RF planar coils comprise a first data communication coil and a second power receiving coil;
the power receiving coil being operative with a capacitor and a voltage regulator for generating and supplying power to the IC; and
the capacitor is coupled to the IC using conductive vias.

8. A system comprising:
a chip comprising:
an integrated circuit (IC) being embedded in a frontplane layer and comprising a plurality of amplifiers configured to amplify received neural signals from a monitored subject, and a radio data signal generator configured to process the amplified neural signals and generate a multiplexed digital signal;
radio-frequency (RF) planar coils embedded in a backplane layer and electrically connected to the IC, the RF planar coils being configured for wireless transmission of the multiplexed digital signal and being configured to receive wireless power signals to power the IC; and
a plurality of on-chip electrodes integrated with the frontplane layer and configured to directly sense the neural signals of the subject and provide the neural signals to the plurality of amplifiers; and
a prosthetic device having coupled thereto a computing device and an external power source and configured to be worn by the subject wherein the computing device receives the multiplexed digital signal and the external power source supplies the wireless power signals to the prosthetic device, wherein the prosthetic device comprises one or more actuators that are controlled based on the sensed neural signals from the plurality of on-chip electrodes;
wherein the chip comprising the frontplane layer, the backplane layer and the plurality of on-chip electrodes form a wireless, battery-less monolithically-integrated neural interface (MINI) device configured to be implanted.

9. The system of claim 8, wherein the chip further comprising conductive vias for electrically connecting the IC to the RF planar coils.

10. The system of claim 9, wherein each conductive vias comprising a through-silicon via.

11. The system of claim 9, wherein the integrated circuit comprises a top layer and a bottom layer, wherein the conductive vias are generally coupled to the top layer on opposite sides of the bottom layer.

12. The system of claim 8, wherein each on-chip electrode of the plurality of on-chip electrodes comprising a tungsten core and a gold plating surrounding the tungsten core.

13. The system of claim 8, wherein the plurality of on-chip electrodes comprising one of a pillar electrode array and a planar electrode array.

14. The system of claim 13, wherein the plurality of on-chip electrodes comprises one of 1000 electrodes and 1024 electrodes.

15. The system of claim 8, wherein
the RF planar coils comprise a first data communication coil and a second power receiving coil;
the power receiving coil being operative with a capacitor and a voltage regulator for generating and supplying power to the IC; and
the capacitor is coupled to the IC using conductive vias.

16. A method comprising:
manufacturing a chip for a wireless, battery-less monolithically-integrated neural interface (MINI) device, the manufacturing the chip comprising:
embedding an integrated circuit (IC) comprising a plurality of amplifiers configured to amplify received neural signals from a monitored subject in a frontplane layer;
embedding a radio data signal generator configured to process the amplified neural signals and generate a multiplexed digital signal; and
embedding a radio-frequency (RF) planar coils in a backplane layer, the RF planar coils being electrically connected to the IC and configured for wireless transmission of the multiplexed digital signal to a remote wireless device and being configured to receive wireless power signals to power the IC; and
on-chip integrating a plurality of on-chip electrodes on the chip, the plurality of on-chip electrodes configured to directly sense the neural signals of the subject and provide the neural signals to the plurality of amplifiers, wherein on-chip integrating comprises forming one of a pillar electrode array or a planar electrode array, and wherein the plurality of on-chip electrodes comprises at least 1000 electrodes.

17. The method of claim 16, further comprising forming a conductive vias for electrically connecting the IC to the RF planar coils.

18. The method of claim 17, wherein each conductive vias comprising a through-silicon via.

19. The method of claim 17, wherein the integrated circuit comprises a top layer and a bottom layer, wherein the conductive vias are generally coupled to the top layer on opposite sides of the bottom layer.

20. The method of claim 16, wherein the on-chip integrating of the plurality of on-chip electrodes includes for each on-chip electrode of the plurality of on-chip electrodes comprising forming a tungsten core and plating the tungsten core with gold plating surrounding the tungsten core.

21. The method of claim 16, wherein the on-chip integrating of the plurality of on-chip electrodes includes forming one of a pillar electrode array and a planar electrode array.

22. The method of claim 21, wherein the plurality of on-chip electrodes comprises one of 1000 electrodes and 1024 electrodes.

* * * * *